US006090608A

United States Patent [19]
Oppenheim et al.

[11] Patent Number: 6,090,608
[45] Date of Patent: Jul. 18, 2000

[54] SV-40 DERIVED DNA CONSTRUCTS COMPRISING EXOGENOUS DNA SEQUENCES

[75] Inventors: Ariella Oppenheim; Nava Dalyot; Orly Ben-Nun-Shaul; Deborah Rund; Ziv Sandalon; Toba Chajek-Shaul; Shulamit Metzger, all of Jerusalem, Israel

[73] Assignees: Yissum Research Development Company of the Hebrew University of Jerusalem; Hadasit Medical Research Services and Development Company Limited, both of Jerusalem, Israel

[21] Appl. No.: 08/737,047

[22] PCT Filed: May 4, 1995

[86] PCT No.: PCT/US95/05595

§ 371 Date: Jan. 15, 1997

§ 102(e) Date: Jan. 15, 1997

[87] PCT Pub. No.: WO95/30762

PCT Pub. Date: Nov. 16, 1995

[30] Foreign Application Priority Data

May 4, 1994 [IL] Israel ........................................ 109558

[51] Int. Cl.[7] .............................. C12N 7/01; C12N 15/86; C12N 5/10
[52] U.S. Cl. .................................. 435/235.1; 435/320.1; 435/325; 435/455; 536/23.5
[58] Field of Search ................................. 536/23.1, 23.5; 435/320.1, 235.1, 325; 514/44; 424/93.1, 93.21

[56] References Cited

U.S. PATENT DOCUMENTS

| | | | |
|---|---|---|---|
| 4,396,601 | 8/1983 | Salser et al. | 424/94 |
| 5,399,346 | 3/1995 | Anderson et al. | 424/93.21 |

OTHER PUBLICATIONS

Pondel et al. The LCR–like alpha–globin positive regulatory element functions as an enhancer in transiently transfected cells during erythroid differentiation. Nucleic Acids Research, vol. 20, No. 2, pp. 237–253, Jan. 25, 1992.

Oppenheim et al. A cis–acting DNA signal for encapsidation of simian virus 40. J. Virol. vol. 66, No. 9, pp. 5320–5328, Sep. 1992.

Sambrook et al. eds. Molecular Cloning A laboratory Manual 2nd edition. pp. 16.18, 1989.

Orkin et al. Report and recommendations of the panel to assess the NIH investment in research on gene therapy. Distributed by the National Institutes of Health, Bethesda, MD., USA, Dec. 7, 1995.

Crystal, R. Transfer of genes to humans: Early lessons and obstacles to success. Science. vol. 270, pp. 404–410, Oct. 20, 1995.

Chaudhary, P.M. and Roninson, I.B., "Expression and Activity of P–Glycoprotein, a Multidrug Efflux Pump, in Human Hematopoietic Stem Cells," *Cell*, 66:85–94 (1991).

Rubin, E.M., et al., "Inhibition of Early Atherogenesis in Transgenic Mice by Human Apolipoprotein Al," *Nature*, 353:265–267 (1991).

Sorrentino, B.P., et. al., "Selection of Drug–Resistant Bone Marrow Cells In Vivo After Retroviral Transfer of Human MDR1," *Science*, 257:99–103 (1992).

Graham, F.L., et al., "Characteristics of a Human Cell Line Transformed by DNA From Human Adenovirus Type 5," *J. Gen. Virol.*, 36:59–72 (1977).

Frei, E., et. al., "Bone Marrow Autotransplantation for Solid Tumors—Prospects," *J. Clin. Onc.*, 7(1) :515–526 (1989).

Fojo, A.T., et al., "Expression of a Multidrug–Resistance Gene in Human Tumors and Tissues," *Proc. Natl. Acad. Sci. USA*, 84:265–269 (1987).

Chajek–Shaul, T., et al., "Expression of the Human Apolipoprotein A–I Gene in Transgenic Mice Alters High Density Lipoprotein (HDL) Particle Size Distribution and Diminishes Selective Uptake of HDL Cholesteryl Esters," *Proc. Natl. Acad. Sci. USA*, 88:6731–6735 (1991).

Armitage, J.O. and Gale, R.P., "Bone Marrow Autotransplantation," *Am. J. Med.*, 86:203–209 (1989).

Breslow, J.L., "Genetic Basis of Lipoprotein Disorders," *J. Clin. Invest.*, 84:373–380 (1989).

Ueda, K., et al., "Expression of a Full–Length cDNA for the Human "MDR1" Gene Confers Resistance to Colchicine, Doxorubicin, and Vinblastine," *Proc. Natl. Acad. Sci. USA*, 84:3004–3008 (1987).

(List continued on next page.)

*Primary Examiner*—Jasemine C. Chambers
*Assistant Examiner*—Deborah J. R. Clark
*Attorney, Agent, or Firm*—Hamilton, Brook, Smith & Reynolds, P.C.

[57] ABSTRACT

The invention relates to DNA constructs comprising an exogenous DNA sequence encoding a therapeutic protein product or itself a therapeutic product, DNA sequences derived from SV40 for replication and packaging of said construct into pseudovirions, and a DNA sequence encoding one or more regulatory elements sufficient for the expression of said therapeutic protein in a mammalian cell operatively linked thereto. The therapeutic product integrated into the DNA constructs of the invention can be a protein selected from the group consisting of enzymes, receptors, structural proteins, regulatory proteins and hormones. Of particular interest are β-globin, P-glycoprotein and apolipoprotein A-I. Specific DNA constructs are plasmids pSO6β-9, pSO6β-1, pSO41, pSM1, and pSAIc. The invention also relates to SV40 pseudovirions containing a DNA construct according to the invention, which are capable of infecting and being expressed in mammalian cells. Also within the scope of the invention are transduced mammalian cells having integrated into their genome a DNA construct according to the invention, said cells being capable of expressing the therapeutic protein product. The invention also relates to a method for in vivo and ex vivo treatment of an individual suffering from an acquired or hereditary pathological disorder, in which a therapeutic product is not made by said individual, or is made in abnormally low amounts or in a defective form or is normally made in physiological amounts to be increased by employing the DNA construct, pseudovirions or transduced cells of the invention.

29 Claims, 23 Drawing Sheets

OTHER PUBLICATIONS

Podda, S., et. al., "Transfer and Expression of the Human Multiple Drug Resistance Gene into Live Mice," *Proc. Natl. Acad. Sci. USA*, 89:9676–9680 (1992).

Noonan, K.E., et. al., "Quantitative Analysis of MDR1 (Multidrug Resistance) Gene Expression in Human Tumors by Polymerase Chain Reaction," *Proc. Natl. Acad. Sci. USA*, 87:7160–7164 (1990).

Winocour, E., et. al., "Modulation of the Cellular Phenotype by Integrated Adeno–Associated Virus," *Virology*, 190:316–329, (1992).

Wright, S., et al., "Regulated Expression of the Human β–Globin Gene Family in Murine Erythroleukaemia Cells," *Nature*, 305:333–336 (1983).

Plump, A.S., et al., "Human Apolipoprotein A–I Gene Expression Increases High Density Lipoprotein and Suppresses Atherosclerosis in the Apolipoprotein E–Deficient Mouse," *Proc. Natl. Acad. Sci. USA*, 91:9607–9711 (1994).

Paszty, C., et al., "Apolipoprotein AI Transgene Corrects Apolipoprotein E Deficiency–Induced Atherosclerosis in Mice," *J. Clin. Invest*, 94:899–903 (1994).

Karlsson, S., et. al., "Expression of the Human β–Globin Gene Following Retroviral–Mediated Transfer into Multipotential Hematopoietic Progenitors of Mice," *Proc. Natl. Acad. Sci. USA*, 85:6062–6066 (1988).

Gordon, D.J. and Rifkind, B.M., "High–Density Lipoprotein—The Clinical Implications of Recent Studies," *N. Engl. J. Med.*, 321(19) :1311–1316 (1989).

Miller, D.G., et al., "Gene Transfer by Retrovirus Vectors Occurs Only in Cells That Are Actively Replicating at the Time of Infection," *Mol. and Cell. Biol.*, 10(8) :4239–4242 (1990).

Grosveld, F., et al., "Position–Independent, High–Level Expression of the Human β–Globin Gene in Transgenic Mice," *Cell*, 51:975–985 (1987).

Mikisch, G.H., et. al., "Transplantation of Bone Marrow Cells From Transgenic Mice Expressing the Human MDR1 Gene Results in Long–Term Protection Against the Myelosuppressive Effect of Chemotherapy in Mice," *Blood*, 79(4) :1087–1093 (1992).

Pastan, I. and Gottesman, M.M., "Multidrug Resistance," *Annu. Rev. Med.*, 42:277–286 (1991).

Ward, M., et. al., "Transfer and Expression of the Human Multiple Drug Resistance Gene in Human CD34+ Cells," *Blood*, 84(5) :1408–1414 (1994).

Dalyot, N. and Oppenheim, A., "Efficient Transfer of the Complete Human Beta–Globin Gene into Human and Mouse Hemopoeitic Cells Via SV40 Pseudovirions," In: Gene Transfer and Gene Therapy, (Alan R. Liss, Inc.) 47–56 (1989).

Klimecki, W.T., et al., "P–Glycoprotein Expression and Function in Circulating Blood Cells From Normal Volunteers," *Blood*, 83(9) :2451–2458 (1994).

Delaflor–Weiss, E., et. al., "Transfer and Expression of the Human Multidrug Resistance Gene in Mouse Erythroleukemia Cells," *Blood*, 80(12) :3106–3111 (1992).

Walsh, C.E., et. al., "Regulated High Level Expression of a Human γ–Globin Gene Introduced Into Erythroid Cells by an Adeno–Associated Virus Vector," *Proc. Natl. Acad. Sci. USA*, 89:7257–7261 (1992).

Fojo, A.T., et al., "Amplification of DNA Sequences in Human Multidrug–Resistant KB Carcinoma Cells," *Proc. Natl. Acad. Sci. USA*, 82:7661–7665 (1985).

Karathanasis, S.K., et al., "Isolation and Characterization of Human Apolipoprotein A–I Gene," *Proc. Natl. Acad. Sci. USA*, 80:6147–6151 (1983).

Grodzicker, E. and Hopkins, N., (1981) "Origins of Contemporary DNA Tumor Virus Research," In: J. Tooze (ed.), *DNA tumor viruses*, (NY: Cold Spring Harbor Laboratory) 1–60 (1982).

Schaefer, E.J., et al., "Genetic High Density Lipoprotein Deficiency," In: N.E. Miller (ed.), *High Density Lipoproteins and Atherosclerosis II*, (Elsevier Science Publ. B.V.) 79–87 (1989).

Hanaia, E., et al., "cDNA for the Multidrug Resistance (MDR–1) Gene in a Transcription Unit of a Safety Modified Retrovirus Confers In Vivo Resistance to Taxol on Early Precurser Cells in a Mouse Transplant Model and on Long–Term Culture," *Blood* 82 (Suppl): 216A, Abstract No. 848 (1993).

Ward, M., et al., "Transfer and Expression of the Multiple Drug Resistance (MDR) Gene into Human Hematopoietic Cells," *Blood*, 80(Suppl) :239a (1992).

Chang, J.C., et al., "A 36–Base–Pair Core Sequence of Locus Control Region Enhances Retrovirally Transferred Human β–Globin Gene Expression," *Proc. Natl. Acad. Sci. USA*, 89:3107–3110 (1992).

```
          TGTTATTTTTTACTTGGACTCTTGTGGGGAATAAGATACATGTTTTATTCTTATTTATGA
    8301  ---------+---------+---------+---------+---------+---------+ 8360
          ACAATAAAAATGAACCTGAGAACACCCCTTATTCTATGTACAAAATAAGAATAAATACT

TTCAAGCACTGAAAATAGTGTTTAGCATCCAGCAGGTGCTTCAAAACCATTTGCTGAATG
    8361  ---------+---------+---------+---------+---------+---------+ 8420
          AAGTTCGTGACTTTTATCACAAATCGTAGGTCGTCCACGAAGTTTTGGTAAACGACTTAC

ATTACTATACTTTTTACAAGCTCAGCTCCCTCTATCCCTTCCAGCATCCTCATCTCTGAT
    8421  ---------+---------+---------+---------+---------+---------+ 8480
          TAATGATATGAAAAATGTTCGAGTCGAGGGAGATAGGGAAGGTCGTAGGAGTAGAGACTA
                     ↓
          TAAATAAGCTTCAGTTTTTCCTTAGTTCCTGTTACATTTCTGTGTGTCTCCATTAGTGAC
    8481  ---------+---------+---------+---------+---------+---------+ 8540
          ATTTATTCGAAGTCAAAAAGGAATCAAGGACAATGTAAAGACACACAGAGGTAATCACTG

CTCCCATAGTCCAAGCATGAGCAGTTCTGGCCAGGCCCTGTCGGGGTCAGTGCCCCACC
    8541  ---------+---------+---------+---------+---------+---------+ 8600
          GAGGGTATCAGGTTCGTACTCGTCAAGACCGGTCCGGGGACAGCCCCAGTCACGGGGTGG

CCCGCCTTCTGGTTCTGTGTAACCTTCTAAGCAAACCTTCTGGCTCAAGCACAGCAATGC
    8601  ---------+---------+---------+---------+---------+---------+ 8660
          GGGCGGAAGACCAAGACACATTGGAAGATTCGTTTGGAAGACCGAGTTCGTGTCGTTACG

TGAGTCATGATGAGTCATGCTGAGGCTTAGGGTGTGTGCCCAGATGTTCTCAGCCTAGAG
    8661  ---------+---------+---------+---------+---------+---------+ 8720
          ACTCAGTACTACTCAGTACGACTCCGAATCCCACACACGGGTCTACAAGAGTCGGATCTC
```

FIG. 1C

```
        TGATGACTCCTATCTGGGTCCCCAGCAGGATGCTTACAGGGCAGATGGCAAAAAAAAGGA
8721    ---------+---------+---------+---------+---------+---------+ 8780
        ACTACTGAGGATAGACCCAGGGGTCGTCCTACGAATGTCCCGTCTACCGTTTTTTTTCCT

GAAGCTGACCACCTGACTAAAACTCCACCTCAAACGGCATCATAAAGAAAATGGATGCCT
8781    ---------+---------+---------+---------+---------+---------+ 8840
        CTTCGACTGGTGGACTGATTTTGAGGTGGAGTTTGCCGTAGTATTTCTTTTACCTACGGA
                                ↓
        GAGACAGAATGTGACATATTCTAGAATATATTATTTCCTGAATATATATATATATATATA
8841    ---------+---------+---------+---------+---------+---------+ 8900
        CTCTGTCTTACACTGTATAAGATCTTATATAATAAAGGACTTATATATATATATATATAT

TACACATATACGTATATATATATATATATATATATTTGTTGTTATCAATTGCCATAGAAT
8901    ---------+---------+---------+---------+---------+---------+ 8960
        ATGTGTATATGCATATATATATATATATATATATAAACAACAATAGTTAACGGTATCTTA

GATTAGTTATTGTGAATCAAATATTTATCTTGCAGGTGGCCTCTATACCTAGAAGCGGCA
8961    ---------+---------+---------+---------+---------+---------+ 9020
        CTAATCAATAACACTTAGTTTATAAATAGAACGTCCACCGGAGATATGGATCTTCGCCGT

GAATCAGGCTTTATTAATACATGTGTATAGATTTTTAGGATCTATACACATGTATTAATA
9021    ---------+---------+---------+---------+---------+---------+ 9080
        CTTAGTCCGAAATAATTATGTACACATATCTAAAAATCCTAGATATGTGTACATAATTAT

TGAAACAAGGATATGGAAGAGGAAGGCATGAAAACAGGAAAAGAAAACAAACCTTGTTTG
9081    ---------+---------+---------+---------+---------+---------+ 9140
        ACTTTGTTCCTATACCTTCTCCTTCCGTACTTTTGTCCTTTTCTTTGTTTGGAACAAAC

CCATTTTAAGGCACCCCTGGACAGCTAGGTGGCAAAAGGCCTGTGCTGTTAGAGGACACA
9141    ---------+---------+---------+---------+---------+---------+ 9200
        GGTAAAATTCCGTGGGGACCTGTCGATCCACCGTTTTCCGGACACGACAATCTCCTGTGT

TGCTCACATACGGGGTCAGATCTGACTTGGGGTGCTACTGGGAAGCTCTCATCTTAAGGA
9201    ---------+---------+---------+---------+---------+---------+ 9260
        ACGAGTGTATGCCCCAGTCTAGACTGAACCCCACGATGACCCTTCGAGAGTAGAATTCCT

TACATCTCAGGCCAGTCTTGGTGCATTAGGAAGATGTAGG
9261    ---------+---------+---------+--------+ 9300
        ATGTAGAGTCCGGTCAGAACCACGTAATCCTTCTACATCC
```

FIG. 1D 0.1 Multiplicity of Infection 0.3 Multiplicity of Infection 0.1 Multiplicity of Infection 0.3 Multiplicity of Infection

FIG. IIA
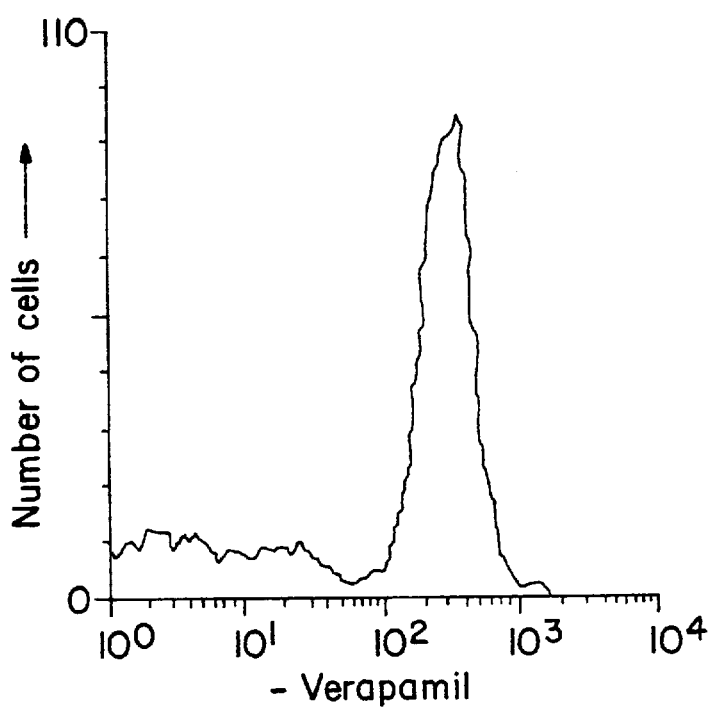
FIG. IIB
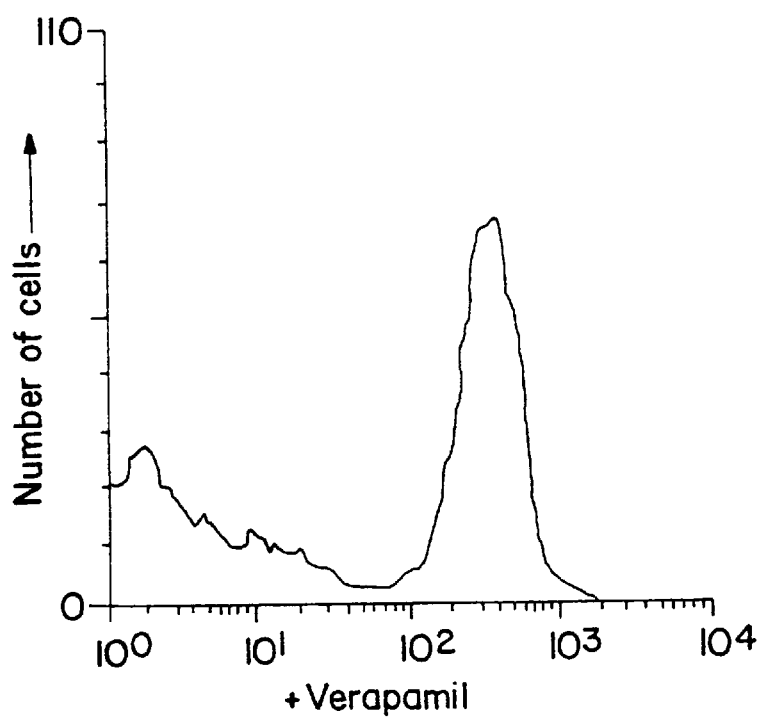

− Verapamil

+ Verapamil

SV-40 DERIVED DNA CONSTRUCTS COMPRISING EXOGENOUS DNA SEQUENCES

RELATED APPLICATIONS

This application is the U.S. National Phase Application of PCT/US95/05595 with an international filing date of May 4, 1995 and which is a continuation-in-part application of Israel Patent Application No.: 109558, filed May 4, 1990, entitled "SV40 Derived DNA Constructs Comprising Exogenous DNA Sequences," the teachings of which are hereby incorporated by reference, in their entirety.

FIELD OF THE INVENTION

The present invention is generally directed to gene therapy, and particularly to gene therapy of hemopoietic diseases. More specifically, the present invention relates to DNA constructs comprising exogenous DNA encoding a therapeutic protein product, DNA sequences derived from SV40 and additional genetic regulatory elements sufficient for the expression of the exogenous DNA in cells of a mammal, thereby enabling the obtention, once the constructs are inserted therein, of transfected mammalian cells which are capable of expressing the exogenous DNA encoding the therapeutic product.

BACKGROUND OF THE INVENTION

The concept of gene therapy first arose during the 1960s and early 1970s. As it became clear that active genes may be transferred into mammalian cells, the idea that diseases may be treated at the genetic level started to develop. In many hereditary diseases the patient suffers from low or altogether absent production of a critical protein. The rationale behind gene therapy approach is that the missing protein may be supplied by the appropriate gene, encoding the specific protein, introduced into the patient's cells. This rationale may be applied to any protein of therapeutic value, for example the production of tumor suppressors in the treatment of cancer. Furthermore, this approach is also applicable to the production of regulatory macromolecules such nucleic acids which would bind to a biologically active protein or block its expression.

There are two basic strategies, generally ex vivo and in vivo gene therapy. Ex vivo gene therapy may be described as genetically modifying cells obtained from a patient, or from a different source, and using the modified cells to treat a pathological condition which will be improved by the long-term or constant delivery of the therapeutic product produced by the modified cells. Treatment includes also the re-introduction, where applicable, e.g. in the case of erythroid cells, of the modified cells, obtained from either the patient or from a different source, into the patient. In vivo gene therapy, on the other hand, refers to direct in vivo delivery of the therapeutic gene into the appropriate tissue of the patient. In vivo delivery may be achieved by a variety of techniques, such as intravenous delivery, direct injection into muscles, inhalation into the lung, etc.

With respect to the specific case of treating β-thalassemia, i.e. gene therapy with the normal β-globin gene, a number of developments have been achieved. The molecular defects of β-thalassemia have been well characterized and seem amenable to genetic correction. In β-thalassemia patients, deficient or absent β-globin gene synthesis causes the production of poorly hemoglobinized, defective erythrocytes resulting in severe anemia. Effective gene therapy requires safe, efficient, and stable transfer of globin genes into human hemopoietic stem cells and subsequent high-level gene expression in maturing erythroid cells. Prior to clinical trials, it was necessary to develop experimental laboratory and animal models. Such models would enable the detailed study of the target cells and the regulation of the inserted gene.

One of the major problems in developing a model for gene therapy of β-thalassemia is the difficulty in introducing the cloned plasmid DNA into hemopoietic cells. Several procedures have been developed to circumvent this difficulty. However, none has been successful in achieving gene delivery and expression. For example, attempts have been made to insert the β-globin gene into retrovirus-derived vectors and subsequently to infect multi-potential hemopoietic progenitors of murine erythroid cells [see Karlsson, S., et al., (1988) Proc. Natl. Acad. Sci. USA 85:6062–6066]. While β-globin expression was obtained in the transduced animals and cells, this system using retrovirus-derived vectors is undesirable for several reasons. Use of retrovirus-derived vectors would be inefficient with human cells and incompatible with non-dividing cells [Miller, D. G., et al., Mol. Cell. Biol. (1990) 10(8):4239–4242] and also causes massive rearrangements when LCR elements are included [Chang, J. C., et al., (1992) Proc. Natl. Acad. Sci. 89:3107–3110]. Additionally, retroviral vectors may present a health hazard if applied to human gene therapy, because the introduction of retrovirus DNA sequences with their potent regulatory elements can lead to the undesired, hazardous expression of non-globin genes in erythroid cells.

Use of adeno-associated vectors for the introduction of a human γ-globin gene into erythroid cells has also been performed [Walsh, C. E., et al., (1992) Proc. Natl. Acad. Sci. USA 89:7257–7261] with successful expression of the γ-globin gene. However, it was recently found that adeno-associated virus (AAV) interferes with normal cellular regulation [Winocour, E., et al., Virology (1992) 190:316–329].

In contrast, the present invention provides for the first time, an SV40-derived vector encoding, for example β-globin, that can be effectively introduced into human erythroid cells, for example erythroid cells from β-thalassemia patients, and be expressed therein at high levels to provide approximately normal levels of β-globin, thereby providing a way for the gene therapy treatment of β-thalassemia. The SV40-derived vectors have a number of advantages over the adeno-derived vectors or the retrovirus-derived vectors, the major ones being the safety of using SV40 for human administration, the ease of manipulation of SV40 vectors and the possibility to prepare SV40 pseudovirions for infection of erythroid cells.

The constructs of the invention may also be useful in delivering P-glycoprotein, encoded by the human MDR1 gene, in bone marrow autografting. As will be shown, the SV40 pseudoviral vector is most promising for ex vivo (and probably also in vivo) gene therapy via the bone marrow (BM), most probably an excellent vector for the treatment of bone marrow autografts. Such autografting procedures with MDR1 transfer are already approved for use in the United States.

The autografting of hemopoietic stem cells from bone marrow or peripheral blood to rescue patients from high dose chemotherapy has been explored intensively in lymphomas, Hodgkin's Disease, and solid tumors [Armitage J. and Gale R (1989) Am J Med 86:203–209; Frei E., et al., (1989) J Clin Oncol 7:515]. The major limitation of conventional bone marrow autografting is that the patient is still left for a period of several weeks without a functional bone marrow during the chemotherapy-induced nadir at which time, mortality and morbidity are high. A promising approach to avert this problem is the conferring of chemotherapy resistance to the patients' own BM cells prior to treatment. These cells then repopulate the BM and allow the administration of more intense, curative chemotherapy. An additional benefit anticipated from chemotherapy-resistant autografting (besides lowering patient mortality) is the need for fewer days in hospital and less need for antibiotics. This would greatly lower the overall cost of the autotransplantation procedure, which is is an important consideration in these days of concern over the rising costs of health care.

A major hinderance to performing gene therapy is the lack of an efficient procedure for introducing cloned DNA into primary human cells. Gene transfer using viral infection, in particular using retroviral vectors, has been widely applied as a solution to this problem. Retroviral vectors are efficient vectors for murine cells. However, as already mentioned above, many problems have been encountered in their use with human cells, in particular with stem cells. These will be discussed in detail below. In addition, there are well-founded fears regarding the use of retroviral vectors as to their potential for inducing malignancies in recipient cells. This concern is based on the fact that the natural sources of these viruses are various animal tumors.

The MDR1 gene [Pastan I. and Gottesman M. (1991) Ann Rev Med 42:277–286] encodes a 170 kd plasma transmembrane glycoprotein (P-glycoprotein), which confers energy-dependent resistance to a number of naturally-occurring, structurally unrelated types of chemotherapeutic agents, including anthra-cyclines, vinca alkaloids, epipodophyllotoxins, taxol, and actinomycin D [Pastan and Gottesman (1991) ibid.]. Although this gene was first identified in tumor cells which overexpresssed P-glycoprotein (Fojo A., et al., (1985) Proc Natl Acad Sci USA 82:7661–7665], the MDR1 gene product is expressed in normal body tissues, at variable levels. These range from very high levels in kidney tubule and colonic epithelium cells to very low levels in most human peripheral blood white blood cells [Fojo, A., et al. (1987) Proc Natl Acad Sci USA 84:265–269; Klimecki W. T., et al., (1994) Blood 83:2451–2458].

It was recently recognized that a small population of normal human BM cells also express MDR1, which are probably stem cells [Chaudhary P, Roninson I (1991) Cell 66:85–94]. A subset of normal peripheral blood lymphocytes which express the CD56 surface antigen have also been found to express high levels of MDR1 (Klimecki et al. (1994). ibid.] However, the overall expression and/or the total number of MDR1-expressing cells in normal human bone marrow and peripheral blood is necessarily low, since this tissue is so highly chemosensitive [Noonan K, et al., (1990) Proc Natl Acad Sci USA 87:7160–7164]. Recent evidence has shown a lack of functional P-glycoprotein in normal granulocytes [Klimecki et al. (1994) ibid.]. This forms the basis for MDR1 gene transfer experiments.

Recent experiments in tissue culture cells showed that a cDNA for the human MDR1 gene conferred resistance to cytotoxic agents [Ueda K, et al., (1987) Proc Natl Acad Sci USA 84:3004–3008; delaFlor-Weiss E, et al., (1992) Blood 80: 3106–3111]. Transgenic mice expressing a human MDR1 gene showed long-term resistance to chemotherapy-induced neutropenia [Mikisch G., et al. (1992) Blood 79:1087–1093]. In another work, murine BM cells expressing human MDR1 were also resistant to chemotherapy-induced neutropenia [Sorrentino B, et al., (1992) Science 257:99–103]. In a further work, live mice transduced with an MDR1 gene showed expression of the gene in granulocytes and in bone marrow cells [Podda S., et al., (1992) Proc Natl Acad Sci USA 89:9676–9680]. All these experiments were performed using retroviral vectors. New retroviral vectors have been developed [delaFlor-Weiss, E. et al. (1992) ibid.; Ward, M., et al. (1992) Blood 80:(Suppl):239a] but as yet, low titers and low transduction efficiency are still a problem, as demonstrated in human tissue culture cells [delaFlor-Weiss et al. (1992) ibid.; Podda et al. (1992) ibid.].

Additional recent experiments have been reported using retroviral vectors [Hanania, E. et al. (1993) Blood 82(Suppl) :216a; Sorrentino B, et al. (1993) Blood 82(Suppl):216a; Ward et al. (1993) ibid.]. In these experiments, the retroviral infection was complicated and difficult to perform. Retroviral vectors require dividing cells in which to integrate and the human BM stem cell is not usually in cycle. Therefore, pretreatment of the cells with multiple growth factors (IL6, IL3, and stem cell factor) was required [Ward M, et al. (1994) Blood 84:1408–1414]. This dictated that the number of cells to be infected be reduced to a minimum, thus necessitating the use of columns for separation of CD34 positive cells (Ward et al. (1993) ibid.; Ward et al, (1994) ibid.], which are the putative stem cells in the bone marrow. The requirement for CD34 separation and use of multiple growth factors makes the procedure highly labor intensive and exceedingly costly. Each column for CD34 separation costs many thousands of dollars, as do the cytokines required for stem cell collection and stimulation to allow for retroviral integraton. Some of these cytokines, such as stem cell factor are at present only available in very limited amounts, precluding their therapeutic use in patients. The high cost of the procedure is an important consideration and a major hinderance in planning the broad scale application of such treatments.

These experiments further demonstrated a number of the other problems which are inherent in the use of retroviral vectors. Murine stem cells are usually transduced at low efficiency, and primate stem cells at even lower efficiency [Sorrentino et al. (1992) ibid.]. Using retroviral vectors in human CD34+ cells, a low transfection efficiency (5–9%) was demonstrated [Ward et al. (1993) ibid.]. In murine cells and in long term bone marrow cultures (Hanania et al. (1993) ibid.; Sorrentino et al. (1993) ibid.], LTR elements were required as promoters to provide expression at high levels. Although infectivity of cells was documented, it was generally by use of PCR technique, which will be positive even if only a small number of cells is infected. Furthermore, the group of researchers who performed the most intense RNA analysis discovered that aberrant splicing occured, deleting much of the coding sequence of the MDR1 protein [Sorrentino et al. (1993) ibid.]. This resulted in truncated mRNA products, which reduced the expression of the transfected gene [Sorrentino et al. (1993) ibid.]. This is typical of many previous attempts at using retroviral vectors for gene therapy of other diseases. These vectors are not faithful in their ability to transmit an exogenous gene, and rearrangement or deletion of the gene of interest is a frequent event.

These findings suggest that development of alternative vectors is desirable and the SV40 pseudoviral vector is potentially more suitable for the purpose of MDR1 expression in bone marrow cells.

The constructs of the present invention may also be used in the treatment of APO A-I associated atherosclerosis. Lipid transfer in the circulation is performed via lipoprotein particles which are composed of apoproteins, triglycerides, phospholipids, cholesteryl ester and free cholesterol. The lipoprotein particles are separated by-density, determined by the lipid/protein proportion in the different particles. The lower density particles (LDL, VLDL, and remnant APO B-containing particles) transfer cholesterol and triglycerides from the liver and the intestine to the peripheral tissues. High levels of these particles contribute to the development of atherosclerosis, the leading cause of heart disease.

Results from epidemiological studies indicate a reverse correlation between High Density Lipoprotein (HDL) levels and susceptibility to atherosclerosis [Gordon, D. J., et al. N Engl J Med (1989) 321:1311–1316]. The importance of HDL levels in the development of atherosclerosis has been demonstrated in human and also in animal models: Trials using lipid lowering drugs revealed that an increase in HDL cholesterol was associated with decreased incidence or progression of coronary heart disease (CHD). Families with inherited hyperalphalipoproteinemia syndrome (high HDL concentrations) tend to be protected from CHD, and families with hypoalphalipoproteinemia (low HDL) show high prevalence of CHD. In experiments with animal models cholesterol accumulation in the developing atherosclerotic lesions is affected by HDL levels. A recent study done with transgenic mice overexpressing human APO -AI gene demonstrates a positive correlation between APO -AI levels and HDL cholesterol. The high level of HDL obtained in these mice reduces the rate of development of fatty streaks in the aorta under atherogenic diet [Rubin, E. M., et al. Nature (1991) 353:265–267].

Furthermore, breeding APO E deficient mice which were severely hypercholesterolemic and developed advanced atheroma independent of dietary cholesterol, with human APO A-I transgenic mice did not affect the elevation in plasma cholesterol but an increase in HDL was observed, associated with six-fold decrease in atherosclerosis [Paszty, C., et al. J Clin Invest (1994) 946:899–903; Plump, A. S., et al. Proc Natl Acad Sci USA (1994) 91:9607–9611].

Genetic defects in the synthesis of APO A-I result in very low HDL levels and premature atherosclerosis [Breslow, J. L. J Clin Invest (1989) 84:373–386]. 9% of the patients with premature coronary artery disease (CAD) suffer from hypoalphalipoproteinemia [Schaefer, E. J., et al. Elsevier (1986) 11:79–86]. This familial disorder is characterized by very low HDL-C level, while the level of the other lipoprotein particles remains normal.

Drugs and factors that usually raise HDL-C levels (exercise conditioning, alcohol intake, estrogens and drugs like nicotinic acid and fibrates) proved to be ineffective in these patients, who are at increased risk for early death as a result of heart disease.

As APO A-I levels determine the HDL-C levels, gene therapy with normal APO A-I promises a new therapeutic approach to this problem.

Other advantages of SV40-derived vectors are set forth herein below in detail.

SUMMARY OF THE INVENTION

The present invention relates to DNA constructs comprising an exogenous DNA sequence encoding a therapeutic protein product or itself a therapeutic product, DNA sequences derived from SV40 for replication and packaging of said construct into pseudovirions, and a DNA sequence encoding one or more regulatory elements sufficient for the expression of said therapeutic protein product in a mammalian cell operatively linked thereto.

The exogenous DNA sequence in the DNA constructs of the invention is selected from the group consisting of DNA which encodes a therapeutic protein product which is not made or contained in the said cells or is made or contained in said cells in abnormally low amount, DNA which encodes a therapeutic protein product which is made or contained in said cell in a defective form and DNA which encodes a therapeutic protein product which is made or contained in said cell in physiologically normal amounts.

DNA constructs according to the invention which further comprises at least one DNA sequence encoding a selectable marker are preferred. Such DNA constructs facilitate the selection of cells into which the exogenous DNA has been incorporated, and/or which express the exogenous DNA after infection with the DNA constructs of the invention.

The mammalian cells are selected from the group consisting of hemopoietic cells, epithelial cells, endothelial cells, liver cells, epidermal cells, muscle cells, fibroblasts, tumor cell and germ line cells.

The hemopoietic cells are preferably bone marrow cells, peripheral and cord blood cells, or liver cells.

The therapeutic product can be a protein selected from the group consisting of enzymes, receptors, structural proteins, regulatory proteins and hormones. In addition, the therapeutic product can be a nucleic acid, for example DNA which binds to a biologically active protein or RNA which inhibits the expression of an essential gene.

The SV40-derived DNA sequences in the constructs of the present invention comprise the ori and ses DNA sequences, and optionally further comprise at least one enhancer for expression, for example the SV40 enhancer. Furthermore, the SV40-derived sequences may also comprise the SV40 polyadenylation signal.

In preferred embodiments the exogenous DNA sequence in the DNA constructs of the invention is a DNA sequence encoding all of or a biologically active fragment of a protein selected from the group consisting of structural proteins and enzymes that are lacking or are defective in hemopoietic disorders such as β-thalassemia, α-thalassemia, sickle cell anemia, anemias due to deficiencies in red blood cell cytoskeletal or membrane proteins or enzymes, deficiencies in heme synthesis enzymes and deficiencies in erythroid transcription factors, particularly DNA encoding human β-globin which is lacking or defective in β-thalassemia or biologically active substitutions, deletions or insertions thereof.

In DNA constructs wherein said exogenous DNA encodes human β-globin, the DNA sequence encoding one or more expression regulatory elements is a DNA sequence encoding a sequence derived from the human β-globin gene cluster locus control element (LCR), preferably the HSII part of the LCR element or a biologically active fragment thereof.

The invention further relates to SV40 pseudovirions containing a DNA construct according to the invention which are capable of infecting and being expressed in mammalian cells. In a particular embodiment the SV40 pseudovirions contain a DNA construct according to the invention in which said exogenous DNA encodes human β-globin and which are capable of infecting and being expressed in human hemopoietic cells. In further particular embodiments said exogenous DNA encodes the human P-glycoprotein or the human apolipoprotein AI.

In a further aspect, the invention relates to transduced mammalian cells having integrated into their genome exogenous DNA sequence encoding a therapeutic protein product or itself a therapeutic product, DNA sequences derived from SV40 for replication and packaging of said construct into pseudovirions, and a DNA sequence encoding one or more regulatory elements sufficient for the expression of said therapeutic protein in a mammalian cell operatively linked thereto, said cell being capable of expressing the therapeutic protein product.

The transduced cells according to the invention can be hemopoietic cells, epithelial cells, endothelial cells, liver cells, epidermal cells, muscle cells, fibroblasts, tumor cells and germ line cells. In preferred embodiments the transduced cells are hemopoietic cells selected from the group consisting of bone marrow cells, peripheral or cord blood cells and liver cells having integrated into their genome exogenous DNA encoding human β-globin.

Also preferred are bone marrow cells or peripheral blood stem cells having integrated into their genome exogenous DNA encoding P-glycoprotein as well as fibroblasts or liver cells having integrated into their genome exogenous DNA encoding apolipoprotein A-I.

The DNA constructs of the invention may further comprise at least one DNA sequence encoding a selectable marker.

In yet a further aspect, the invention relates to a method for ex vivo treating an individual suffering an acquired or hereditary pathological disorder in which a therapeutic product is not made by said individual, or is made in abnormally low amounts or in a defective form or is normally made by said individual in physiological amount which needs to be increased comprising providing DNA construct according to the invention; obtaining cells from an individual suffering said genetic disorder and optionally culturing said cells under suitable conditions and testing the cells for sufficient gene transfer and expression; infecting the thus obtained, optionally cultured cells with said DNA construct; selecting from the thus infected cells which express the exogenous DNA carried in the said DNA construct and culturing said selected cells under suitable conditions; and reintroducing the selected cultured cells into said individual. In other embodiments the methods of the invention may be used to increase the expression of a therapeutic product which is normally expressed in physiological amount.

This therapeutic method of the invention may be used for ex vivo treatment of hereditary diseases, malignant diseases, bacterial and viral infectious diseases, autoimmune diseases or allergy.

Of particular preference is a method for ex vivo treating hemopoietic disorders comprising providing DNA constructs according to the invention in which said exogenous DNA encodes human β-globin or functional substitutions, deletions or insertions thereof; obtaining hemopoietic cells from an individual suffering a hemopoietic disorder selected from the group consisting of bone marrow cells, peripheral and cord blood cells and optionally culturing said cells under suitable conditions; testing the cells for sufficient gene transfer and expression; infecting the thus obtained, optionally cultured cells with the said DNA constructs; selecting from the infected cells which express the exogenous DNA carried by the DNA constructs and culturing said selected cells under suitable conditions; and reintroducing these cultured cells into said individual.

Also of preference are methods of increasing drug resistance in autografting of hemopoietic bone marrow cells or peripheral blood stem cells, employing said exogenous DNA the human MDR1 gene, or treatment of atherosclerosis, employing the human APO A-I gene.

The invention also relates to a method of treating an individual suffering a hereditary or acquired pathological disorders by administering to said individual a DNA construct according to the invention, wherein said exogenous DNA encodes a therapeutic protein product which is not made or contained in the cells of said individual or is made in abnormally low amounts or is made or contained in the cells of said individual in a defective form, by administering to said individual transduced cells according to the invention which have integrated thereinto such DNA constructs. Of special interest are methods for treatment of hemopoietic disorders, particularly β-thalassemia, increasing drug resistance in autografting hemopoietic cells and treatment of APO A-I associated atherosclerosis.

Still further, the invention provides pharmaceutical compositions for treating hereditary or acquired disorders comprising suitable DNA constructs according to the invention or transduced cells according to the invention and phramaceutically acceptable carriers, diluents or excipients. Of particular interest are compositions for treating hemopoietic disorders, especially β-thalassemia and for treating APO A-I associated atherosclerosis.

DNA constructs according to the invention which further comprises at least one DNA sequence encoding a selectable marker are also encompassed within the framework of the invention. Such DNA constructs facilitate the selection of cells into which the exogenous DNA has been incorporated, and/or which express the exogenous DNA after infection with the DNA constructs of the invention.

BRIEF DESCRIPTION OF THE DRAWINGS

FIG. 1(c) and (d) shows the nucleotide sequence of the HSII fragment of LCR element; arrows indicate the fragment incorporated into the vectors shown in FIGS. 1(a) and 1(b), from the HindIII site at coordinate 8486 to the XbaI site at coordinate 8860 (374 bp);

DETAILED DESCRIPTION OF THE INVENTION

Figure 1A:
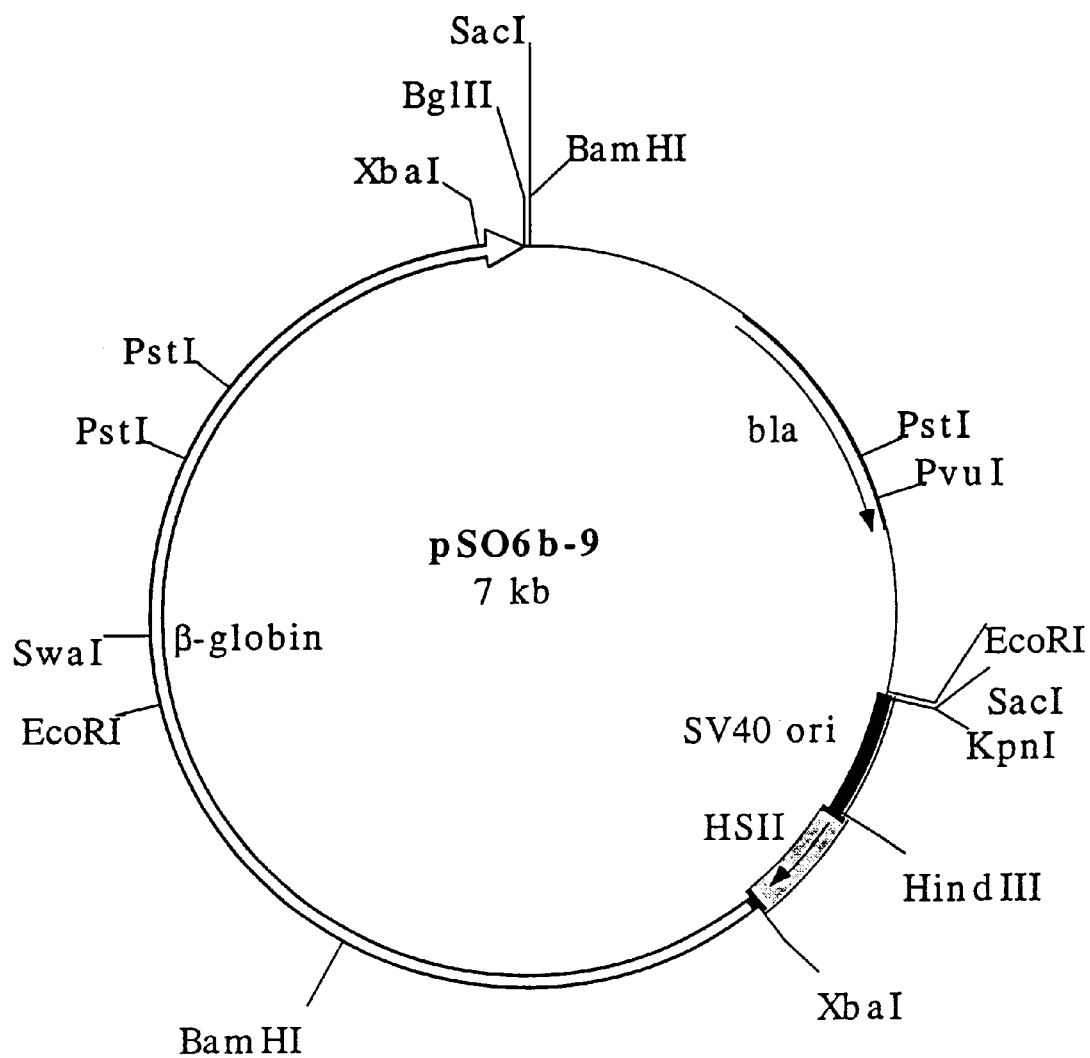
FIG. 1(a) is a schematic representation of the circularized configuration, including the various structural and regulatory elements and restriction map, of the vector pSO6β-9, as described in Example 1.

The present invention is based on the obtention, after considerable effort which is described hereafter and particularly in Example 1 of a DNA vector encoding β-globin that is capable of being packaged (encapsidated) into infectious SV40 pseudovirions and following infection thereby of human erythroid cells which lack normal β-globin expression, derived from β-thalassemia patients, is capable of expressing large amounts of normal β-globin.

The reasons for choosing SV40 and the advantages thereof are briefly as follows: SV40 is a papovirus that grows lytically in African Green Monkey kidney (AGMK) cells. Its genome is circular double stranded DNA 5.4 kb. During the early phase after infection it produces the T-antigens. The large T-antigen activates viral DNA replication by binding at the viral ori. Late in the infection cycle the late viral proteins, VP1, VP2 and VP3, which form the viral capsid, are produced. The viral DNA becomes encapsidated and mature virion particles are liberated into the medium as the cell lyses. Gene delivery of the gene of choice, e.g. β-globin, into the target cells of choice, e.g. hemopoietic cells, is based on encapsidation of plasmid DNA as SV40 pseudovirions (see below). The DNA is then transmitted into the target cells via viral infection. Encapsidation is preferably performed in COS (monkey kidney) cells which express SV40 T-antigen constitutively [Gluzman, Y. (1981) Cell 23:175–182].

Thus, the vectors that have been developed, in accordance with the present invention, carry the SV40 origin of replication (ori) and packaging signal (ses) to facilitate replication and packaging of plasmid in the COS cells. The SV40 capsid proteins are supplied in trans by a helper SV40 DNA, cotransfected into the COS cells.

Further, the SV40 vector is suitable for gene therapy as well as for studying the regulation of cloned genes in hemopoietic cells, because: (a) the molecular biology of SV40 is well understood; (b) viral stocks of relatively high titer can be prepared and can be easily monitored for titer and purity; (c) SV40 has a very wide, perhaps unlimited, host range, including human bone-marrow (BM) cells; (d) the vector for efficient gene transfer is very small: only about 200 bp of the SV40 genome encompassing the origin of replication (ori and ses sequences) are required and thus minimal interference with target cell gene regulation is expected; and (e) SV40 is probably harmless to man, since it was originally discovered as a contaminant in the polio vaccines n the USA in the 1950's, with the result that millions of people were thus inadvertently immunized with SV40. From random testing it is known that many people carry antibodies to SV40, but, however, no harmful effects of the virus have ever been observed [Grodzicker, T. and N. Hopkins (1981) Origins of Contemporary DNA Tumor Virus Research. In: DNA tumor viruses. J. Tooze ed. Cold Spring Harbor Laboratory, New York. 1–60 (1982)].

Moreover, the early studies by the present inventors with the prokaryotic cat gene as a reporter gene, demonstrated that the SV40 vector is very efficient in gene delivery into human hemopoietic cells, including fresh bone marrow cells [Oppenheim, A., et al., (1986) Proc. Natl. Acad. Sci. USA 83:6925–6929]. These studies, however, did not provide means for the delivery and expression of therapeutic genes, e.g. the human β-globin gene, into cells lacking normal β-globin expression.

Subsequently, the present inventors cloned the complete human β-globin gene into a plasmid vector that carries the SV40 ori and ses, yielding the plasmid pSO6β-1 [Dalyot, N. and A. Oppenheim (1989)] Efficient transfer of the complete human β-globin gene into human and mouse hemopoietic cells via SV40 pseudovirions. In: Gene Transfer and Gene Therapy A. L. Beaudet, R. Mulligan and I. M. Verma, eds. Alan R. Liss, Inc. New York, 47–56]. After removing the bacterial sequences from the pSO6β-1 plasmid, the resulting plasmid, called SO6β-1 was encapsidated as an SV40 pseudovirion and transmitted into cultured mouse (MEL) and human (K562) hemopoietic cells by viral infection. High levels of non-integrated copies of the transmitted β-globin gene in Hirt supernatant of the infected cells 48 hours post-infection were found, but, however, β-globin expression was very low [Dalyot and Oppenheim, ibid.].

It should be noted that in the pSO6β-1 the β-globin gene was cloned in opposite orientation to the SV40 early promoter, since the plasmid was designed to utilize the authentic regulatory signals of the β-globin gene for β-globin expression. Thus, the low β-globin expression of this vector may have been due to antisense RNA, produced from the SV40 promoter.

Additional regulatory elements, 50 kb upstream to the β-globin gene [Grosveld, F., et al., (1987) Cell 51:975–985] were discovered. These control elements, which surround 4 erythroid-specific nuclease hypersensitive sites (HSI to HSIV) were found to confer high level, position independent, erythroid specific expression to the β-globin gene. They were first cloned as very large fragments of approximately 20 kb. Further studies in several laboratories indicated that a small fragment of approximately 0.8 kb, surrounding HSII, was sufficient for the induction of high level β-globin expression [see, for example, Chang et al., ibid.; Novak et al. ibid.]. However, it should be noted that the above noted use of the HSII fragment (also called LCR for locus control region—Chang et al., ibid., or LAR for locus activation region—Novak et al., ibid.) for enhanced β-globin expression was in a system using retrovirus-based vectors which were transferred into a murine cell line. This system encountered many difficulties. For example, incorporating LAR determinants in retroviral vectors promoted gross viral rearrangement [Chang et al., ibid.]. Novak et al. [ibid.] mention that "inclusion of LAR determinants in retroviral vectors also entails the potential risk of activating the expression of non-globin genes in erythroid cells". Moreover, none of said studies entailed human primary cell cultures.

Based on the inventors' earlier findings on SV40-derived constructs, and on the subsequently discovered additional control elements, the DNA constructs of the invention have been developed.

Thus, the present invention relates to a DNA construct comprising an exogenous DNA sequence encoding a therapeutic protein product or itself a therapeutic product, DNA Sequences derived from SV40 for replication and packaging of said construct into pseudovirions, and a DNA sequence encoding one or more regulatory elements sufficient for the expression of said therapeutic protein in a mammalian cell operatively linked thereto.

More particularly the invention relates to a DNA construct comprising an exogenous DNA sequence encoding a therapeutic protein product selected from the group consisting of DNA which encodes a therapeutic protein product which is not made or contained in the said cells or is made or contained in said cells in abnormally low amount, DNA which encodes a therapeutic product which is made or contained in said cell in a defective form and DNA which encodes a therapeutic protein product which is normally made or contained in said cell in physiological amounts, DNA sequences derived from SV40 for replication and packaging of said construct into pseudovirions, and a DNA sequence encoding one or more regulatory elements sufficient for the expression of said therapeutic protein in a mammalian cell operatively linked thereto.

The mammalian cells in which said exogenous DNA is expressed can be hemopoietic cells, epithelial cells, endothelial cells, liver cells, epidermal cells, muscle cells, fibroblasts, tumor cells and germ line cells.

The therapeutic products encoded by the exogenous DNA sequence can be proteins of therapeutic value such as, for example, enzymes, receptors, structural proteins, regulatory proteins and hormones or a nucleic acid of therapeutic value, such as, for example, DNA which would bind to a protein or RNA which would block the expression of a protein.

The SV40-derived DNA sequences in the DNA constructs of the invention comprise the ori and ses DNA sequences, and optionally further comprise the SV40 enhancer. DNA constructs carrying as little as 200 bp of SV40, ori and ses, can be efficiently packaged. Including enhancer elements, for example the SV40 enhancer, while not necessary for packaging, may improve expression of the inserted gene.

In a particular embodiment, the invention relates to a DNA construct comprising an exogenous DNA sequence encoding all of or a biologically active part of a protein selected from the group consisting of structural proteins and enzymes that are lacking or are defective in hemopoietic disorders such as β-thalassemia, α-thalassemia, sickle cell anemia, anemias due to deficiencies in red blood cell cytoskeletal or membrane proteins or enzymes, deficiencies in heme synthesis enzymes and deficiencies in erythroid transcription factors, DNA sequences derived from SV40 for replication and packaging of said construct into pseudovirions, and a DNA sequence encoding one or more regulatory elements sufficient for the expression of said therapeutic protein in a hemopoietic cell operatively linked thereto.

In this particular embodiment the hemopoietic cells can be bone marrow cells, peripheral and cord blood cells, or liver cells.

In a preferred embodiment, the DNA construct according to the invention comprise exogenous DNA sequence which encodes human β-globin which is lacking or defective in β-thalassemia or functional substitutions, deletions or insertions thereof.

As discussed above, and demonstrated in the following examples, in the DNA constructs comprising exogenous DNA which encodes the human β-globin gene, or functional analogues thereof, the DNA sequence encoding one or more β-globin expression regulatory elements is a DNA sequence encoding a sequence derived from the human β-globin gene cluster locus control element (LCR). More particularly, the human β-globin LCR-derived sequence is the HSII part of the LCR element or a biologically active fragment thereof. A specific biologically active fragment of HSII is a 334 bp fragment, from the HindIII site at coordinate 8486 to the XbaI site at coordinate 8860, illustrated in FIG. 1(c) and (d).

Figure 1B:
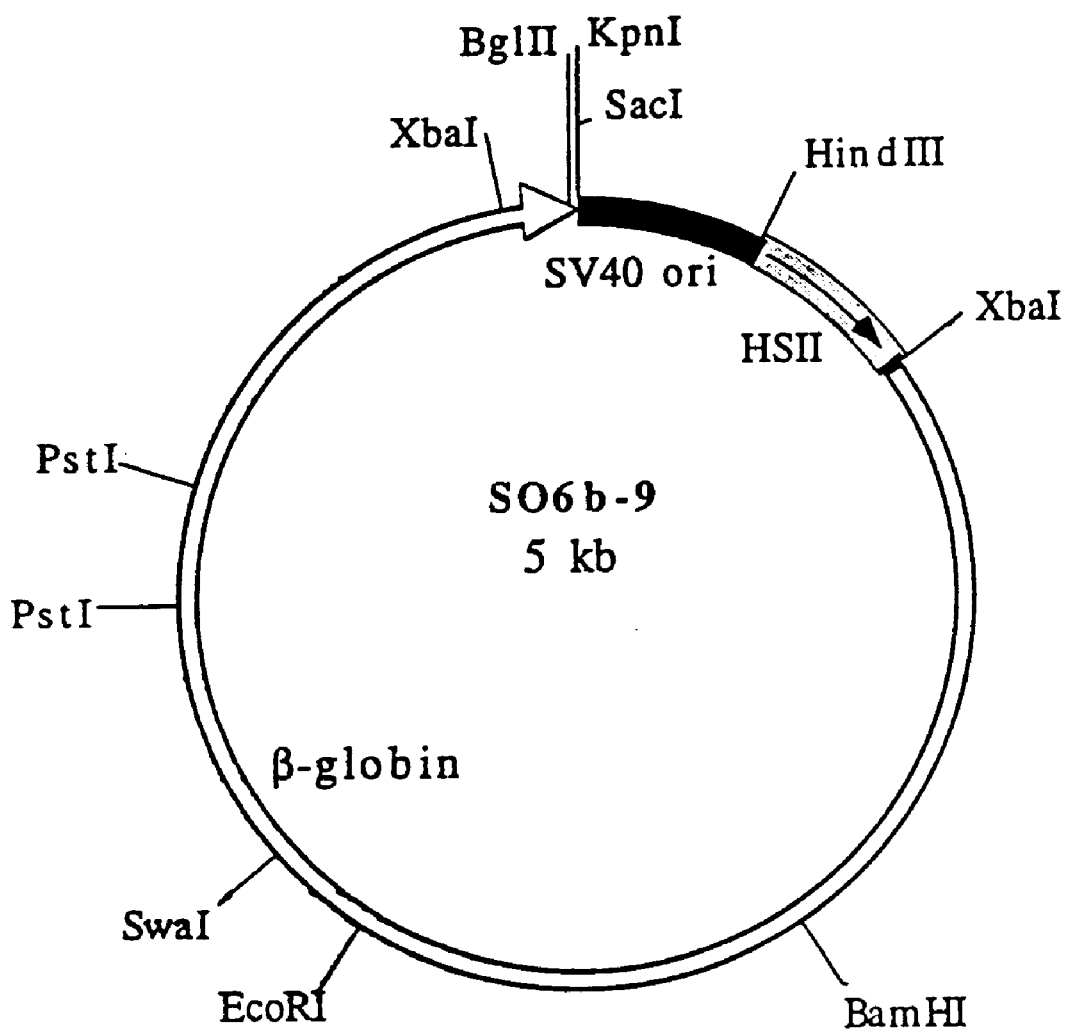
FIG. 1(b) is a schematic representation of the circularized configuration, including the various structural and regulatory elements and restriction map, of the vector SO6β-9, as described in Example 1.

Such specific DNA constructs are the vector pSO6β-9, depicted in FIG. 1(a), deposited at the ATCC under Accession No. 75596 on Oct. 27, 1993 and the vector SO6β-9, depicted in FIG. 1(b).

These specific DNA constructs are capable of being packaged into infectious SV40 pseudovirions, and following infection thereby of human erythroid cells obtained from β-thalassemia patients, which lack normal β-globin expression, are capable, as will be shown in the following Examples, of expressing large amounts of normal human β-globin in these cells. The exogenic DNA sequence encoding human β-globin can be replaced by a different exogenous DNA sequence encoding another therapeutic protein, or itself a therapeutic product. For example, such another exogenous DNA sequence can be a sequence encoding normal structural proteins or enzymes which are known to be lacking or are known to be defective in various hemopoietic disorders such as β-thalassemia, sickle cell anemia, anemias due to deficiencies in red blood cell cytoskeletal proteins or enzymes, disorders due to deficiencies in heme synthesis enzymes and deficiencies in specific regulatory proteins such as erythroid specific transcription factors.

In addition to the above DNA constructs, the invention relates to particular constructs in which said SV40-derived sequences comprise, in addition to said ses and ori DNA sequences, and the SV40 enhancer, also the SV40 polyadenylation signal. An example of such construct is the plasmid pSO41, shown in FIG. 14, deposited at the American Type Culture Collection under No. ATCC 97126, deposited Apr. 28, 1994, in accordance with the provisions of the Budapest Treaty. These constructs which contained the SV40 polyadenylation signal are designed so that said exogenous DNA (the gene of interest) can be cloned between the SV40 early promoter, embedded in the SV40 ori region, and the SV40 polyadenylation signal. This facilitates cloning of cDNA or any open reading frame (ORF) for expression. RNA transcription is initiated at the SV40 early promoter. The polyadenylation signal serves for cleavage and polyadenylation of the transcribed RNA. Translation occurs from the translation initiation codon (ATG) in the cloned cDNA, or from an ATG introduced in frame at the beginning of the cloned ORF. As will be shown in the following Examples, and particularly with reference to the human MDR1 gene, the addition of the polyadenylation signal substantially improved expression of the cloned gene.

Apart from exogenous DNA encoding a therapeutic protein product related to the hemopoietic system, DNA constructs of the present invention may comprise exogenous DNA encoding any desired therapeutic product with DNA sequencers encoding suitable regulatory elements sufficient for the expression of said therapeutic product in a mammalian cell operatively linked thereto. Examples of such additional therapeutic products are enzymes, e.g. adenosine deaminase (ADA), gluco-cerebrosidase and hexoaminidase; receptors, e.g. low density lipoprotein receptor (LDL receptor) and IL-6 receptor; transporters, e.g. cystic fibrosis transmembrane conductance regulator (CFTR) and multi-drug resistance (MDR); structural proteins, e.g. LDL and APO A-I; regulatory proteins, e.g. P53 and retinoblastoma (Rb); hormones, e.g. insulin, growth hormone; and growth factors, e.g. IL-2 and IL-6.

The preparation of such DNA constructs encoding any of the therapeutic products is within the capabilities of the man skilled in recombinant DNA techniques [see, for example Sambrook, J. et al., (1989) Molecular Cloning, A Laboratory Manual, Cold Spring Harbor Laboratory Press, Cold Spring Harbor, N.Y.], by which, for example, the constructs containing the β-globin gene can be manipulated to remove the β-globin gene and insert in its place a gene of choice, encoding the product of choice. The gene sequence encoding the product of choice can be a known sequence or any newly discovered one encoding a therapeutically active product, or a functional analogue thereof. Where necessary, the DNA sequence encoding the regulatory element/s sufficient for the expression of the therapeutic product in a mammalian cell can be replaced by similar techniques.

Thus, in a further preferred embodiment, the invention relates to a DNA construct in which said exogenous DNA is the human MDR1 gene. The importance of enhancing drug resistance has been discussed above, particularly in connection with autografting hemopoietic stem cells. This mammalian gene confers resistance against a variety of drugs such as colchicine, vinblastine, adriamycin and others.

The delivery of the human MDR1 gene with the SV40 constructs of the invention is described in Example 3. A rapid assay was used for detection of the level of MDR1 gene expression in human leukemia and lymphoma cells, using fluorescent activated cell sorter (FACS) analysis of cells stained with rhodamine 123. Rhodamine 123 is a flourescent dye whose efflux from cells is mediated by P-glycoprotein [Chaudhary and Roninson (1991) ibid.]. Many studies have confirmed that the ability to efflux this dye from cells coincides with expression at the RNA and protein levels, of P-glycoprotein [Chaudhary and Roninson (1991) ibid.; Klimecki et al. (1994) ibid.]. Rhodamine staining has the advantage that it is a functional assay, detecting not only that the P-glycoprotein is present but that it is functional. The principle of the assay is as follows: cells incubated with the dye appear brightly stained if they have uptake but no efflux of the dye. On the other hand, cells with the ability to extrude the dye, because they express high levels of P-glycoprotein, are dull-staining. A further confirmation that P-glycoprotein expression is responsible comes from the ability of various substances which are MDR1 inhibitors to prevent the efflux of the dye. Thus, highly MDR1-expressing cells, which are rhodamine-dull, will become rhodamine-bright if they are incubated simultaneously with verapamil, an inhibitor of MDR1 activity. The assay is rapid and reliable and is therefore of great value as a guiding tool in analysis of patient specimens prior to and following chemotherapy for malignant disease. Many studies now use rhodamine staining in parallel to other methods, such as RNA analysis, or alone as a way of defining P-glycoprotein activity [Chaudhary and Roninson (1991) ibid.; Ludescher et al. (1993) ibid.; Klimecki et al. (1994) ibid.].

Various tissue culture lines were also analyzed, using rhodamine staining. These lines have been used as an experimental model system for expression studies in the development of the MDR1 vector. Recently, a report confirms our experience that using rhodamine 123 to evaluate MDR1 gene expression is a valuable screening tool for transfection in gene transfer experiments [Hegewisch-Becker et al. (1993) ibid.].

It has previously been shown in transgenic animals that exogenous MDR1 gene expression can protect against the deleterious effects of chemotherapy. The MDR1-carrying vector according to the invention, expected to be highly effective at infecting human BM cells may thus be applied to human cancer therapy. The development of new viral vectors for gene therapy is a prerequisite for progress in this field. Because of the limits of retroviral integration into dividing cells, the lack of long term expression in most human systems studied to date is not surprising.

At present, it is apparent that the extreme difficulty of performing MDR1 gene transfer via retroviral infection makes this methodology very impractical for any but limited application. In contrast, SV40/MDR1 viral gene therapy will allow the treatment of significant number of patients who fail conventional dose chemotherapy for various malignancies. Therefore, the SV40/MDR1 pseudo-virions may have enormous clinical applications in the field of cancer therapy. It is anticipated that the technique of conferring chemotherapy resistance to normal BM cells expressing physiological levels of P-glycoprotein will be used in the future in combination with other strategies to treat cancer patients (with many types of malignancies) who could benefit from high dose chemotherapy.

As discussed above, the constructs of the present invention may be useful in delivering the human APO A-I gene to patients suffering various coronary diseases, particularly atherosclerosis. Experiments demonstrating the delivery of the APO A-I gene by the present SV40 constructs are described in Example 4.

Additionally, the DNA constructs of the invention may further comprises a DNA sequence encoding at least one selectable marker. Such a selectable marker would enable the post-infection selection of cells which express the exogenous DNA comprised in the DNA construct. For example, the additional DNA sequence can be the bacterial hygromycin B phosphotransferase, hyg or hph, which confers resistance to hygromycin B, the bacterial neomycin resistance gene, neo, which confers resistance to the drug G418, the mammalian multidrug resistance gene, MDR1, which confers resistance against a variety of drugs such as colchicine, vinblastine, adriamycin and others and the mammalian dihydrofolate reductase gene, DHFR, which confers resistance against methotraxate. The selectable marker enables the identification and selection of cell which express the desired exogenous DNA. Use of the selectable markers will be discussed in more detail below.

For use in therapy, the DNA constructs of the invention are preferably first incorporated into SV40 pseudovirions (as described in the Examples), which, thus introduced, represent highly efficient means for inserting the DNA constructs into mammalian cells, i.e. via viral infection of the cells.

Thus, in a further aspect the present invention provides SV40 pseudovirions containing a DNA construct selected from any of the above DNA constructs of the invention which are capable of infecting and being expressed in mammalian cells. These pseudovirions of the invention can be prepared, as detailed herein below, for example by cotransfecting monkey kidney (COS) cells with any of the DNA constructs of the invention and helper SV40 DNA to enable the correct packaging of the DNA constructs into SV40 pseudovirions which are infectious, i.e. capable of infecting mammalian cells, and subsequently being capable of being expressed in the infected cells to provide these cells with the exogenously encoded therapeutic protein product.

In a further aspect the invention relates to a transduced mammalian cell having integrated into its genome exogenous DNA sequence encoding a therapeutic protein product or itself a therapeutic product, DNA sequences derived from SV40 for replication and packaging of said construct into pseudovirions, and a DNA sequence encoding one or more regulatory elements sufficient for the expression of said therapeutic protein in a mammalian cell operatively linked thereto, and optionally a DNA sequence encoding at least one selectable marker, said cell being capable of expressing the therapeutic product.

More particularly, the invention relates to such transduced mammalian cells in which said exogenous DNA sequence is selected from the group consisting of DNA which encodes a therapeutic protein product which is not made or contained in the said cells, DNA which encodes a therapeutic protein product which is made or contained in said cells in abnormally low amount or in a substantially normal amount, or in a defective form and DNA which encodes a therapeutic product which is made or contained in said cells in physiologically normal amounts.

The transduced cell according to the invention can be, for example, hemopoietic cells, epithelial cells, endothelial cells, liver cells, epidermal cells, muscle cells, fibroblasts, tumor cells and germ line cells. In a preferred embodiment of this aspect of the invention the transduced cells are transduced hemopoietic cells such as, for example, bone marrow cells, peripheral or cord blood cells and liver cells, preferably hemopoietic cells in which said exogenous DNA encodes human β-globin.

The invention further provides a method for the ex vivo treatment of an individual suffering an acquired or hereditary pathological condition in which a therapeutic product is not made by said individual, or made is in abnormally low amounts or in a defective form comprising (a) providing a DNA construct according to the invention, optionally comprising a DNA sequence encoding at least one selectable marker; (b) obtaining cells from an individual suffering said genetic disorder and optionally culturing said cells under suitable conditions, and testing the cells for sufficient gene transfer and expression; (c) infecting the thus obtained, optionally cultured cells said DNA construct; (d)(i) culturing all the obtained infected cells under suitable conditions; or (d)(ii) selecting the thus obtained infected cells which express the exogenous DNA carried in the said DNA construct and culturing said selected cells under suitable conditions or and (e) reintroducing the thus obtained cultured cells into said individual.

In case infection of the cells with the DNA construct or pseudovirion of the invention is efficient, it would not always be required to culture the cells in step (d). Moreover, in such cases the use of DNA constructs containing also DNA encoding at least one selectable marker would not be essential. However, in preferred embodiments DNA constructs containing a DNA sequence encoding at least one selectable marker is recommended. For example, cells which have been infected with a DNA construct also comprising the neo, hyg, MDR1 or DHFR genes can be exposed, in step (d)(ii) to G418, hygromycin B, the variety of drugs described above for the MDR1 gene, or methotraxate, respectively, whereby all cells not incorporating the DNA construct used for their infection would be killed prior to re-introduction into the patient. Such markers are suitable for the ex vivo method of the invention.

Testing the infected cells for sufficient expression of the gene can be performed by several techniques. For example, expression of β-globin can be tested at the RNA level, by RT-PCR, as described herein. Testing the infected cells for sufficient gene transfer can be accomplished, for example, by the method described by Oppenhein et al. [Oppenheim, A., et al. Proc. Nat. Acad. Sci. USA (1986) 83:6925–6929 (FIG. 5)].

The method of the invention is suitable for the ex vivo treatment of hemopoietic disorders, particularly β-thalassemia. When thus employed, after providing a DNA construct comprising exogenous DNA encoding a hemopoiesis-related product, particularly human β-globin, or SV40 pseudovirions according to the invention, hemopoietic cells such as bone marrow cells or erythroid cells are obtained from an individual with a hemopoietic disorder, particularly β-thalassemia, and are optionally cultured under suitable conditions. The cells are then infected with the DNA construct or SV40 pseudovirions of the invention as noted above. Further, and if required, the infected cells which express the exogenous DNA sequence carried by the DNA constructs or pseudovirions are selected. The obtained infected, selected infected cells are then cultured under suitable conditions and finally they are re-introduced into said individual having said hemopoietic disorder.

Embodiments of the particularly preferred method of the invention include a method as noted above for treating β-thalassemia, α-thalassemia, sickle cell anemia, anemias due to deficiencies in red blood cell cytoskeletal or membrane proteins or enzymes, deficiencies in heme synthesis enzymes and deficiencies in erythroid transcription factors.

Particularly preferred methods for the treatment of β-thalassemia are those wherein said pseudovirions contain the vector SO6β-9.

The methods of the invention may also be useful in the treatment of atherosclerosis, employing as exogenous DNA the human APO A-I gene, and for increasing drug resistance, employing as exogenous DNA the human MDR1 gene.

The procedures for carrying out each of the steps of the above methods of the invention are set forth in detail herein below (Example 2).

The invention also provides a pharmaceutical composition for treating a hereditary or acquired pathological disorder comprising a therapeutically effective amount of a DNA construct or pseudovirions according to the invention and a pharmaceutically acceptable carrier, diluent or excipient.

Preferred pharmaceutical compositions of the invention are pharmaceutical compositions as noted above for the treatment of β-thalassemia comprising a therapeutically effective amount of pseudovirions containing a DNA construct as above, particularly SV40 pseudovirions containing the vector SO6β-9.

The pharmaceutical compositions of the invention may be prepared by any of the known procedures therefor in which any suitable pharmaceutically acceptable carrier, diluent or excipient may be admixed with the pseudovirions. The preparation of the pharmaceutical compositions of the invention is within the capabilities of the man skilled in the art of pharmacology.

The invention further relates to a method of treating an individual suffering a hereditary or acquired pathological disorder by administering to the individual a therapeutically effective amount of a DNA construct or pseudovirions according to the invention or a pharmaceutical composition according to the invention.

In a preferred embodiment of this in vivo method of treatment the invention provides a method for treating an individual having β-thalassemia by administering to the individual a therapeutically effective amount of pseudovirions containing the vector SO6β-9 or of a pharmaceutical composition containing them.

By the term administration is meant intravenous, intra-arterial, intramuscular, intrathecal, transdermal and intranasal inhalation.

Some of the selectable markers mentioned above may be particularly suitable for use with the in vivo method of treatment of the invention. For example, when the DNA constructs contain a selectable marker such as the MDR1 or DHFR genes, following administration to the patient of the pseudovirions or pharmaceutical composition containing them, the patient may be treated with colchicine, vinblastine, Adriamycin or any other drug to which the cells which have incorporated the DNA construct comprising the MDR1 gene have become resistant, or with methotraxate, in case the DNA construct comprises the DHFR gene. Thus, the desired cells, which will have incorporated the exogenous DNA encoding the desired therapeutic product will survive the drug treatment.

The amount of the pseudovirions or pharmaceutical compositions containing them to be administered to the patient can vary as desired for a therapeutically effective amount and may depend on the patient's age, sex, weight, physical condition, disease or condition to be treated, and other medical criteria as well as on their relative efficacy. This effective amount may be determined by techniques known in the art. For example, in the case of β-thalassemia, m.o.i may be between 1 to 5, so that optimally every cell is infected.

The invention will be described in more detail on hand of the following Examples and the accompanying Figures. The Examples are illustrative only and do not in any sense limit the invention which is only defined by the scope of the appended claims.

EXAMPLE 1

The SV40/β-globin Delivery System (a) Preparation of SV40/β-globin vectors based on SV40 have been developed, for the reasons advantages described above.

On the basis of the above mentioned information, i.e. using the original vectors pSO6β-1 and SO6β-1, and in order to overcome the drawbacks of these earlier vectors, new vectors were prepared which carry an identical fragment of the β-globin gene in both orientations with respect to the SV40 promoter, namely, the vectors pSO6β-2 and pSO6β-3 (Table 1). Both plasmids showed low expression of β-globin when tested in the above noted mouse and human cells, suggesting that a regulatory element was missing from these plasmids.

Following the discovery of the additional regulatory elements, 50 kb upstream to the β-globin gene [Grosveld, F., et al. ibid.], additional new SV40/β-globin vectors were prepared by the present inventors, namely, pSO6β-4 and pSO6β-5 (Table 1). In order to accommodate the HSII element, a fragment of 0.7 kb was first deleted from the upstream region of the cloned gene (i.e. using the pSO6β-2 plasmid as starting material) yielding the plasmid pSO6β-4, this region not carrying any regulatory element [see Wright, S., et al., (1983) Nature 305:333–336]. HSII was then cloned upstream to the gene in pSO6β-4 to yield pSO6β-5 (Table 1). However, it was found that pSO6β-5 does not package as SV40 pseudovirions (packaging efficiency was almost zero). As the only reliable assay for β-globin expression is in erythroid cells, and since efficient gene transmission into erythroid cells required pseudovirions, testing the new constructs for gene expression in erythroid cells was not possible.

It may be noted that the four constructs which do not carry any locus control region (LCR) element, i.e. the HSII fragment, SO6β-1 to β-4, package quite well, yielding pseudovirions at a titer of 105–106 infectious units/ml in a single infection cycle. The pseudoviral titer can be assayed as previously described [Dalyot and Oppenheim, ibid.], by infecting fresh COS cells and analyzing plasmid DNA in the infected cells. This is a quick assay which gives a rough estimate of packaging-efficiency. Alternatively, the titer may be determined more precisely by testing for infectious centers (these are called infection units, or IU) using in situ hybridization. The titer of SO6β-1 pseudovirions obtained by this assay was $2 \times 10^5$ IU/ml (see below).

Having such assays available, it was possible to continue with the development of the above noted vectors to obtain suitable ones, that would be both packageable and capable of expressing β-globin at high levels. Accordingly, additional constructs were prepared in an effort to obtain a packageable SV40/β-globin vector which includes HSII. The inventors considered the possibility that the difficulty in packaging was caused by interactions of the LCR element (i.e. HSII sequence) with other regulatory elements present in the plasmid. Such interactions may lead to a higher order DNA structure which may be incompatible with condensation of the pseudoviral chromatin which is required for packaging. Thus, first the SV40 enhancer was deleted, as its role in erythroid-specific expression in erythroid cells may be unimportant. In this way, pSO7β-5 was constructed by removing one copy of the SV40 enhancer elements from the pSO6β-5 plasmid. However, pSO7β-5 did not package either. The replication of this plasmid was only slightly reduced, which did not account for the dramatic decrease in encapsidation efficiency.

Continuing the same rationale, and in order to better understand the mechanism which interferes with the packaging of the above noted vectors, part of the β-globin 3' enhancer was also removed. Two new plasmids were so constructed, pSO6 β-8 and pSO7β-8, which both lack the β-globin 3' enhancer but differ from one another in having or missing the SV40 enhancer, respectively (see Table 1). Neither of these plasmids was, however, packageable.

In Chang et al. [ibid.], it was disclosed that the 5' region of HSII is more important for the enhancer activity, since it carries several binding sites for transcription factors. The inventors therefore constructed a new plasmid, pSO6β-9 (Table 1), which is derived from pSO6β-5, i.e. it has the SV40 enhancer, and the β-globin 3' enhancer and also lacks the β-globin 5' region, but which carries only 374 bp of the HSII fragment, i.e. about 400 bp of the original HSII sequence in the above earlier plasmid was deleted from the 3' end of this HSII sequence. FIG. 1(a) schematically shows the plasmid pSO6β-9 and its restriction map. pSO6β-9 contains elements from the well known pBR322 bacterial plasmid, from SV40 and the human β-globin gene as follows: The pBR322 fragment is from coordinate 2369 to the EcoRI site at coordinate 4360 (1992 bp) of the pBR322 map. The SV40 fragment is from the HindIII site at coordinate 5171, through the ori region, to the KpnI site at coordinate 294 (366 bp) of the SV40 map. The HSII fragment is from the HindIII site at coordinate 8486 to the XbaI site at coordinate 8860 (374 bp) of the HSII fragment of human β-globin gene cluster sequence (LCR) (the nucleotide sequence of HSII is shown in FIG. 1(c)). The β-globin fragment is from the HincII site at coordinate 61373 to the BglII site at coordinate 65610 (4237 bp) of the human β-globin gene. Thus, pSO6β-9 is a plasmid of 7026 bp which can be propagated in *E. coli* to enable the production of large amounts thereof. SO6β-9 is obtained from pSO6β-9 by removal of the pBR322 fragment, using the SacI sites. SO6β-9 was found to encapsidate in COS cells at a low, but significant efficiency. Thus, pSO6β-9 represents the first β-globin-encoding vector which carries the essential part of the HSII sequence that can be used for expression of β-globin in erythroid cells. A sample of this plasmid, pSO6β-9, has been deposited at the ATCC under Accession No. 75596 (ATCC 75596) in accordance with the provisions of the Budapest Treaty.

SO6β-9 was prepared from pSO6β-9, as depicted in FIG. 1(b). SO6β-9 was constructed by removing the bacterial sequences (pBR322 sequences) from pSO6β-9 by digestion to completion thereof with SacI, followed by SacI inactivation with chloroform treatment, circularization of the large SacI fragment (containing the β-globin gene and the HSII and SV40 fragments) by ligation at a low concentration (1 μg DNA in 200 μl reaction) at 4° C. for about 12 hours (overnight). The circularized DNA was precipitated in 2 volumes of ethanol and resuspended in a low volume of TE buffer. The SO6β-9 plasmid, which lacks bacterial sequences, is considered well suited for gene therapy applications as it contains only human β-globin gene cluster DNA and a minimal amount of SV40 sequences.

TABLE 1

| | SV40/β-globin Vectors | | | | | |
|---|---|---|---|---|---|---|
| Vector | SV40 enhancer[a] | β-globin 5' region[b] | β-globin 3' enhancer[c] | LCR (HSII)[d] | Orientation[e] | Packaging[f] |
| pSO6β-1 | + | + | + | − | ← | very good |
| pSO6β-2 | + | + | + | − | → | good |
| pSO6β-3 | + | + | + | − | ← | good |
| pSO6β-4 | + | − | + | − | → | very good |
| pSO6β-5 | + | − | + | + | → | very poor |
| pSO7β-5 | − | − | + | + | → | poor |
| pSO6β-8 | + | − | − | + | → | poor |
| pSO7β-8 | − | − | − | + | → | poor |
| pSO6β-9 | + | − | + | partial | → | fair |

[a]pSO6 represents vectors which carry the enhancer of SV40 and pSO7 represents those which do not.
[b]The globin 5'-region is from −1.5 kb to −0.8 kb upstream to the gene (BglII to HincII). This region does not have any known regulatory function.

TABLE 1-continued

SV40/β-globin Vectors

| Vector | SV40 enhancer[a] | β-globin 5' region[b] | β-globin 3' enhancer[c] | LCR (HSII)[d] | Orientation[e] | Packaging[f] |
|---|---|---|---|---|---|---|

[c]The β-globin 3' region enhancer has been removed by deleting the sequences beyond the PstI site to the BglII site, 0.6 kb downstream to the poly (A) addition site.
[d]HSII, from HindIII (at coordinate 8486) to coordinate 9269, 51 bp downstream to the BglII site, (783 bp).
[e]Orientation of the β-globin gene is with respect to the SV40 early promoter.
[f]Packaging was assayed by analyzing infected cells for plasmid DNA. This method gives a semi-quantitative estimate of packaging efficiency. pSO6β-1 (very good packaging) gives a titer of $10^5$–$10^6$ infectious units/ml. Poor packaging is when the titer is <$10^2$ IU/ml. Fair packaging is when the titer is about $10^3$–$10^4$ IU/ml.

(b) Encapsidation of plasmid DNA as pseudovirion of SV40

As mentioned above, encapsidation (packaging) of a plasmid to be used for expression in erythroid cells is best carried out in COS cells which constitutively express the SV40 T-antigen. Further, while the vector SO6β-9 carries the SV40 ori and ses sequences to facilitate replication and packaging of the plasmid in the COS cells, SV40 capsid proteins must be provided and these are supplied in trans by a helper SV40 DNA which is co-transfected with the plasmid into the COS cells. Thus, the encapsidation procedure is briefly as follows:

Logarithmically growing COS cells in DMEM medium +10% FCS were co-transfected with 1 ml (per 25 cm$^2$ culture) containing 1.0 μg of plasmid DNA (SO6β-9) and 0.15 μg of SV40 DNA (helper DNA), in DEAE-dextran solution (DEAE-dextran solution in DMEM: 25 mg DEAE-dextran, 2.5 ml Tris-HCl pH 7.0 and 97.5 ml DMEM). 3 ml of the medium were removed after 2 days and the cultures were incubated for 3 more days. Virus stocks were harvested by freeze-thaw 3 times and treated with chloroform. Traces of chloroform were removed with bubbling air and the virion stock stored at −20° C. Mock transfected cultures were similarly treated with DEAE-dextran solution, without DNA. For further concentration, the viral stock was centrifuged through Centricon 30 columns.

(c) Ability of pseudovirions containing SV40/β-globin vectors to infect erythroid cells Two of the above β-globin vectors were used to test for their ability to infect (and subsequently be expressed—see Example 2 below) human erythroid cells. The vectors tested were SO6β-1 (used as a control, as it is known to be able to be packaged and infect erythroid cells—see above) and SO6β-9, which were first introduced into COS cells for the purposes of encapsidation to yield pseudovirions. These tests were important in order to determine both whether the SO6β-9 vector could be successfully packaged (encapsidated) into SV40 pseudovirions that are capable of infecting erythroid cells and whether the LCR regulatory element (HSII fragment), present only in the pSO6β-9 vector, would have the desired effect on β-globin expression while at the same time would not adversely affect packaging and subsequent infection of erythroid cells.

Figure 2:
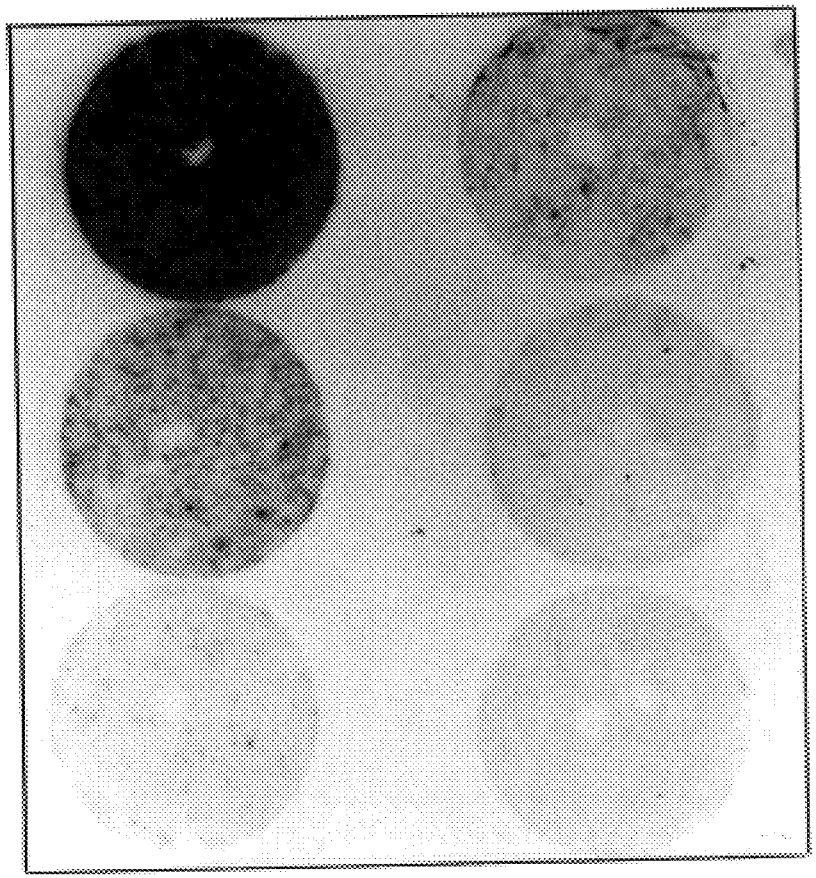
FIG. 2 shows the autoradiographs of hybridized cell culture blots from which the infectivity of pseudovirions containing vectors pSO6β-1 and pSO6β-9 were determined, as described in Example 1.

SV40 pseudovirions containing the above vectors were assayed as infectious units on CMT4, a non-erythroid cell line [Gerard, R. D. and Y. Gluzman (1985) Mol. Cell Biol. 5:3231–3240]. Various dilutions of the pseudovirions were used to infect the CMT4 cells, and two days after infection cell monolayers were transferred onto nitrocellulose membranes, i.e. cell blots were prepared, and were subjected to hybridization with a radiolabeled probe being specific for the vector DNA sequences (for probe, see Example 2 below), the hybridization procedure being essentially the same as that for standard colony hybridization [see Sambrook et al., ibid.]. The results of the titration assays of the SV40 pseudovirions containing the above vectors are shown in FIG. 2, a reproduction of autoradiographs of the infected cell blots. From these blots it was calculated that the titer of the SO6β-1 containing pseudovirions was 2×10$^5$ IU/ml and the titer of the SO6β-9 containing pseudovirions was 1×10$^4$ IU/ml (i.e. 20-fold lower). Thus, while the SO6β-9 vector was not encapsidated as effectively as the SO6β-1 vector to form infectious pseudovirions, it did show a significant amount of encapsidation into infective pseudovirions. These results therefore indicate that the SO6β-9 vector can be effectively introduced into erythroid cells. Subsequently, it was shown that the SO6β-9 vector was expressed at high levels in the erythroid cells to produce significant amounts of β-globin (see Example 2 below). This was in contrast to the SO6β-1 vector which was not effectively expressed in erythroid cells, indicative of the importance of the LCR element in expression of the vector. Accordingly, the SO6β-9 vector may be used as a means for treating β-globin deficiencies, e.g. β-thalassemia patients (see Examples 2 and 3).

EXAMPLE 2

Experimental Model for Gene Therapy of β-thalassemia

A major difficulty in the development of a model for gene therapy of β-thalassemia is the lack of an appropriate human cell line which expresses the adult human β-globin gene. K562 and HEL are human erythroleukemia cell lines that express mostly the fetal and embryonic globin genes. For that reason most of the research in globin expression in other laboratories has been performed in mouse cell lines or in transgenic mice.

For the development of a human experimental model for gene therapy of β-thalassemia, the inventors chose to use a newly developed procedure of a two-step liquid culture procedure that supports the growth and differentiation of human erythroid progenitors [Fibach, E., et al., (1989) Blood 73: 100–103]. In this procedure large scale cultures of erythroid progenitor cells derived from peripheral blood are readily grown. Differentiation of the cultured cells is synchronous, affording detailed investigations of developmentally regulated changes and expression of various genes [Dalyot, N., et al., (1992) Exp. Hematol. 20:1141–1145].

This procedure entails the following main steps: peripheral or cord blood mononuclear cells are first cultured in liquid medium supplemented with hemopoietic growth factors, but not including erythropoietin (Epo). During this phase the early erythroid progenitors, BFUe, proliferate and differentiuate into the more mature progenitors—the CFUe.

The second phase, which results in the exclusive of erythroid cells, depends on the addition of Epo.

Figure 3:
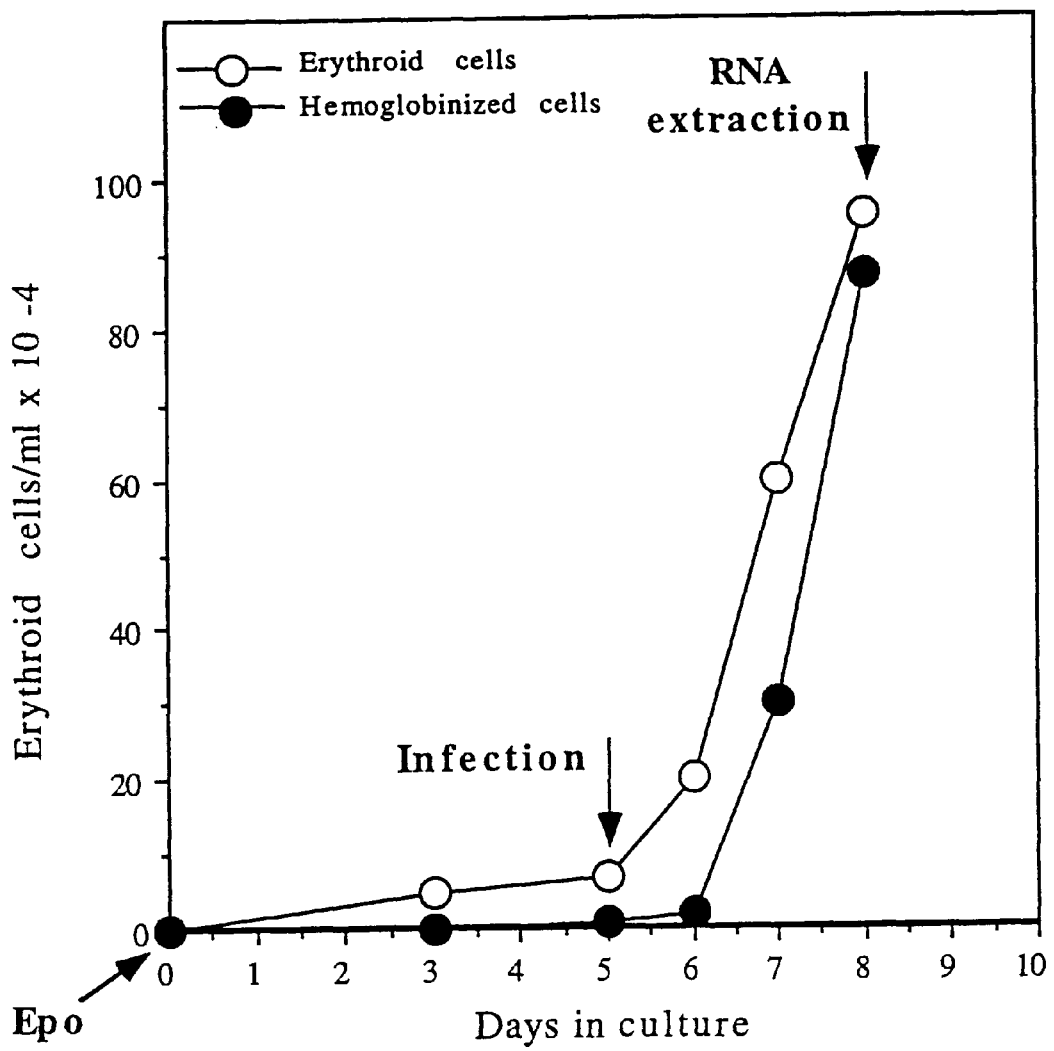
FIG. 3 is a graphic representation of the kinetics of the growth and differentiation of erythroid cells, derived from a β-thalassemia patient, subjected to Epo treatment followed by infection with pseudovirions containing a β-globin encoding vector, as described in Example 2.

Adapting this procedure for the purposes of a model for the gene therapy of β-thalassemia the following procedure was developed: erythroid cells were derived from peripheral blood of $β^0$-thalassemia patients. In the first phase the cells were cultured for 7 days in the absence of Epo. The cells were then transferred to the second phase, and Epo was added. FIG. 3 illustrates the development of the cultures during the second phase, i.e. where the addition of Epo is indicated as being at day 0. Soon after the addition of Epo the erytliroid cells start to proliferate as shown by the open circles. The closed circles represent the number of the hemoglobinized cells which start to appear only at about day 5 after Epo addition. It was previously found that the peak of globin mRNA level is around day 8 [Daylot et al., ibid.]. Therefore, the cultures were infected with β-globin pseudovirions on day 5, and the RNA was harvested on day 8, as indicated in FIG. 3. The β-globin pseudovirions used were those containing the vectors SO6β-1 and SOβ-9 (see Example 1(c) above).

A limiting factor is the number of cells which are available for analysis. It was therefore necessary to develop very sensitive assays for β-globin gene expression. The assay is based on reverse transcription followed by a polymerase chain reaction (RT-PCR). Another important component of the experimental system is the use of cells derived from β-thalassemia patients with known β-globin mutations, which allows to distinguish between RNA produced by the endogenous β-globin gene and the exogenous gene carried by the β-globin pseudovirions.

Figure 4:
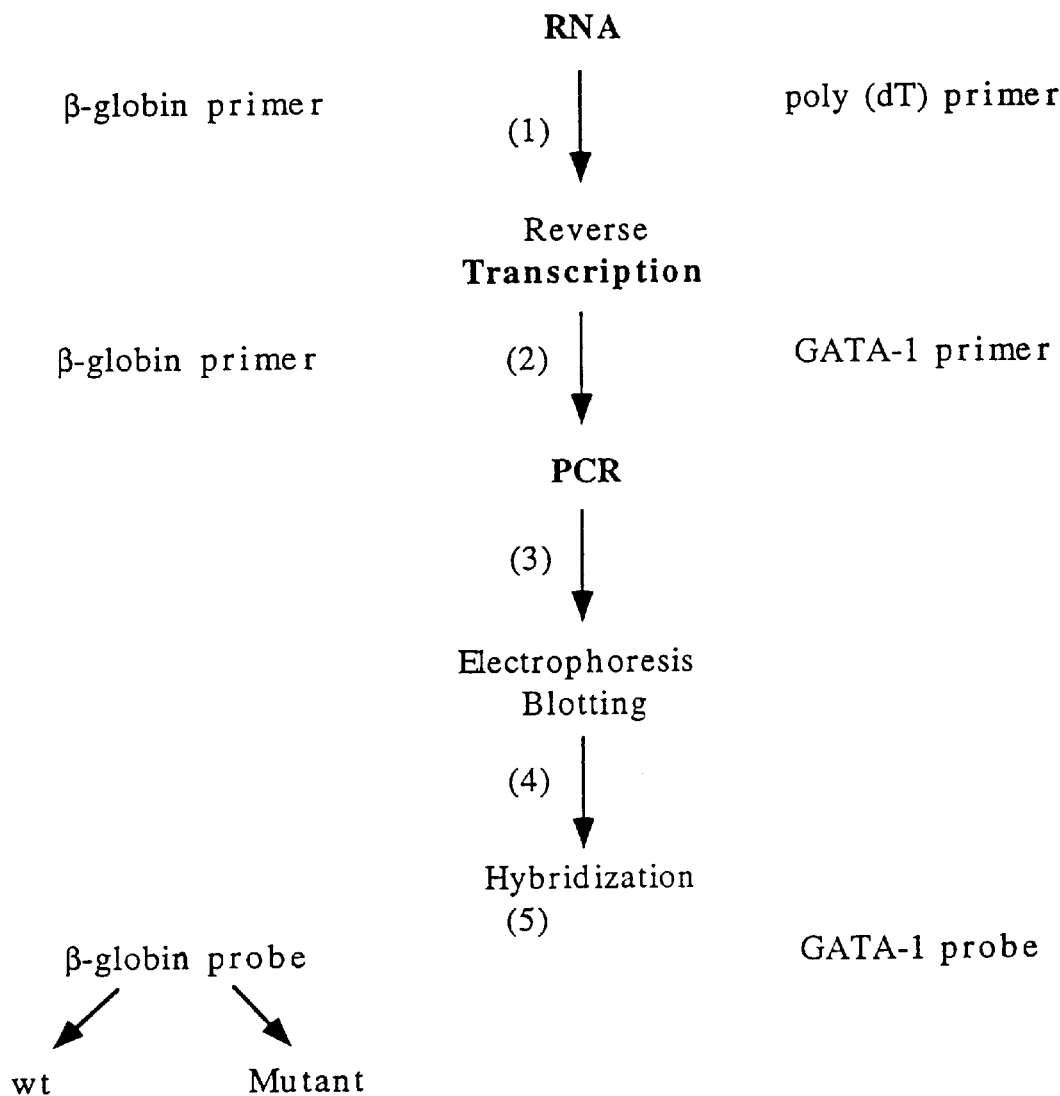
FIG. 4 is a flow-diagram of the procedures used to determine expression of exogenously encoded β-globin in erythroid cells of β-thalassemia patients that were infected with pseudovirions containing-globin encoding vectors.

The experimental design is show in FIG. 4. Since it is known that the β-globin mutation which distinguished between normal and mutant RNA is at the 5' end of the gene, the inventors used, for the reverse-transcription reaction (FIG. 4, step 1), a β-globin specific primer derived from the middle of the gene, with RNA derived from cultures of erythroid cells from β-thalassemia patients being the template. This choice added to the specificity of the test. The resulting cDNA was subjected to PCR (FIG. 4, step 2) and the PCR products were electrophoresed, blotted and finally hybridized to specific oligonucleotide probes (FIG. 4, steps 3–5). Expression of the endogenous β-globin gene was assayed with a mutant-specific probe; the exogenous, normal gene was assayed with the wild type (wt) probe. As an internal standard for erythroid-specific RNA levels, in some experiments, RT-PCR assays of the erythroid-specific gene GATA-1 were used. Reverse transcription was performed on duplicate RNA samples with either β-globin primer or with poly(dT) as a primer. The PCR reaction was performed on the cDNA using β-globin primers or GATA-1 primers. The PCR products were analyzed by hybridization with wild type β-globin probes or with GATA-1 probe (see FIG. 4). All of the above procedures were carried out using the standard methods, well known in the art.

Figure 5A:
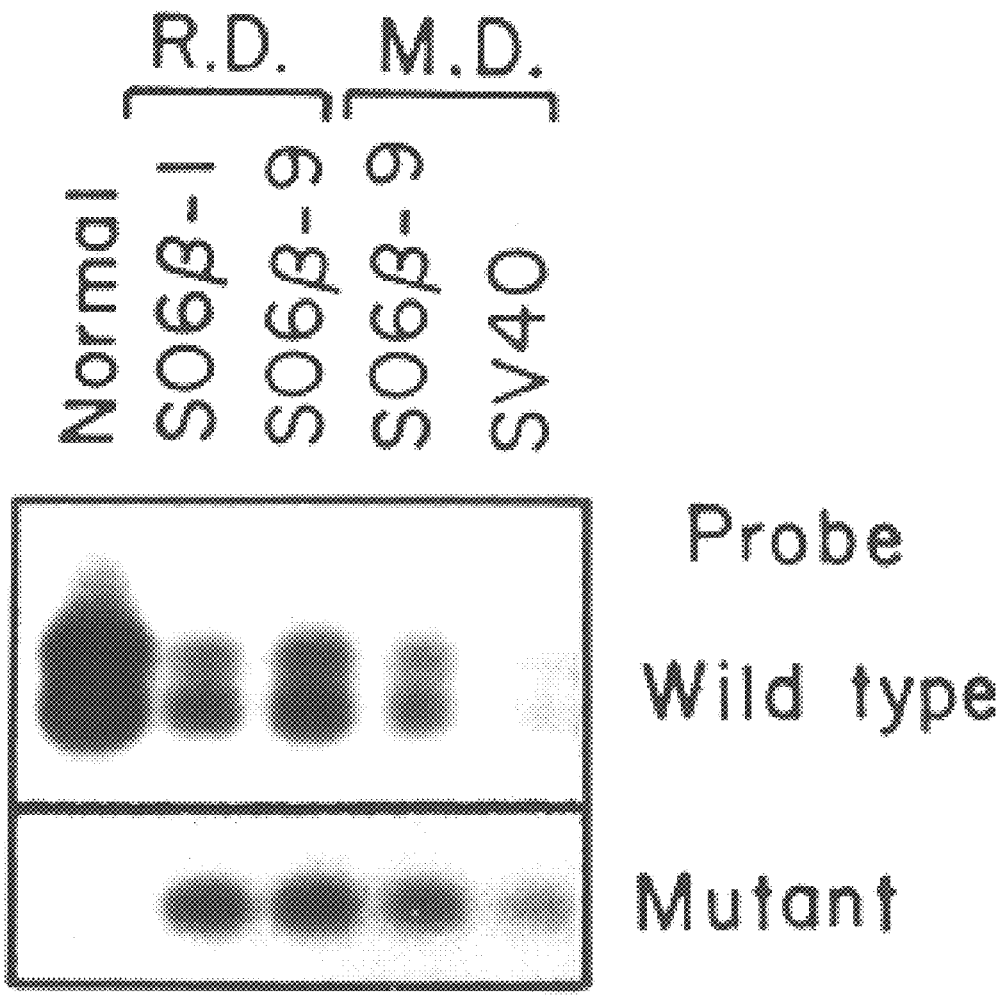
FIG. 5(a) shows autoradiograms of Southern blots of PCR products of reverse-transcribed RNA obtained from erythroid cells of β-thalassemia patients infected with β-globin probes.

FIG. 5(a) shows the results of infection, with the above β-globin pseudovirions, of cultures derived from two patients: R. D. and M. D., who carry the same β-globin mutation, a frameshift in codon 44. The experimental procedures were as noted above, i.e. blood cells were obtained from the patients, cultured (two phases), infected with the β-globin pseudovirions, total RNA was harvested from the infected cells and subjected to the above RT-PCR assay procedure for β-globin expression. It should be noted that infection of the cultures with the pseudovirions was performed with a multiplicity of infection (m.o.i.)=1 for the pSO6β-1 and a m.o.i.=0.1 for the SO6β-9 pseudovirions.

Southern blotting of the PCR products was followed by hybridization with wild type and mutant probes. It can be seen in FIG. 5(a) that RNA harvested from a control normal culture, derived from a non-thalassemic control individual, gave a signal only with the wild type probe. RNA of cultures derived from both patients yielded a low signal with the mutant probe, consistent with previous findings that the endogenous level of the mutated β-globin mRNA in these patients is low.

Intensities of the signals of all cultures with the mutant probe was about equal, demonstrating that equal levels of globin mRNA (and of infected cells) were analyzed. Importantly, the infected cultures showed a significant signal also with the wild type probe, indicating expression of the exogenous, normal β-globin gene. Some signal with the normal probe is also seen in a control infection by SV40 (in cells from patient M. D. only). This is most likely due to cross-reaction with δ-globin mRNA: the δ-globin gene has a high similarity to β-globin; the primers for the RT-PCR and the oligonucleotides probe used in the hybridization recognize the δ-globin gene at almost the same efficiency as β-globin. Nevertheless, in the three cultures infected with β-globin pseudovirions the signal obtained was significantly higher (FIG. 5(a)), demonstrating expression of the normal gene delivered by the β-globin pseudovirions.

It should also be noted that cultures of R. D. were infected with both SO6β-1 and SOβ-9 pseudovirions. The expression signal obtained with SO6β-9 was higher, although the titer of that pseudoviral preparation was 20-fold lower than that of SOβ-1 (Example 1(c)). In fact , because of the low titer, that culture was infected at a multiplicity of 0.1, i.e. at most only 10% of the cells were infected. Nevertheless , as shown in FIG. 5(a), the expression of SO6β-9 is higher than that of SO6β-1 (infected at an m.o.i. of 1). Therefore the presence of the HSII LCR fragment in SO6β-9 has increased the expression of β-globin 20–30 times. Furthermore, the signal of the culture of R. D. infected with SO6β was only 5–10 times lower than that of the normal culture.These results suggest that by increasing the m.o.i. so that every cell is infected, normal level of β-globin gene expression may be achieved.

Figure 5B:
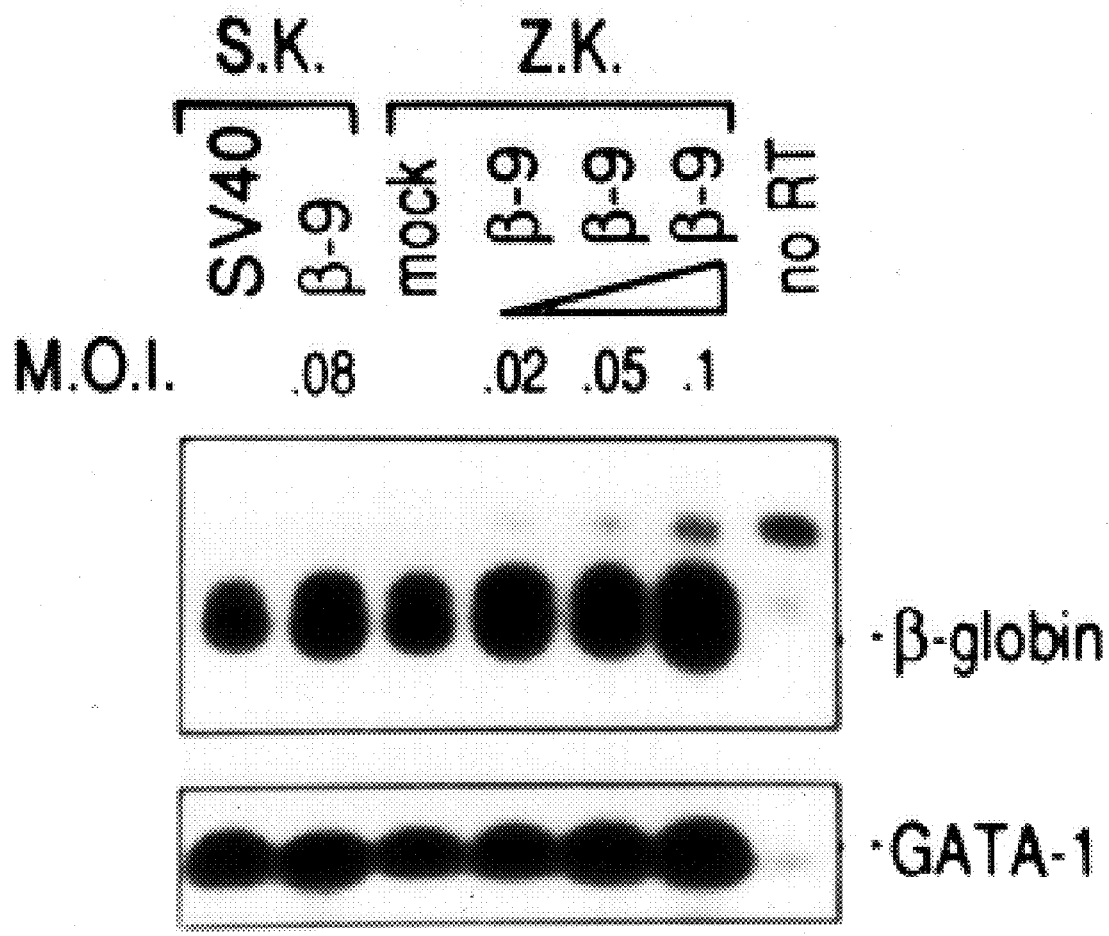
FIG. 5(b) shows representations of autoradiograms of Southern blots containing RNA obtained from erythroid cells of β-thalassemia patients tested with β-globin probes and in which the effects of multiplicity of infection (m.o.i.) of the SO6β-9 containing pseudovirions on β-globin expression were tested.

FIG. 5(b) shows the results of similar infection experiments (using only the pSO6β-9 pseudovirions for test infections) performed with cells derived from two other patients: S. K. and Z. K. As an internal standard for erythroid-specific RNA levels RT-PCR assays of GATA-1 (FIG. 4b) were employed, i.e. using the GATA-1 primers and probe.

Figure 6:
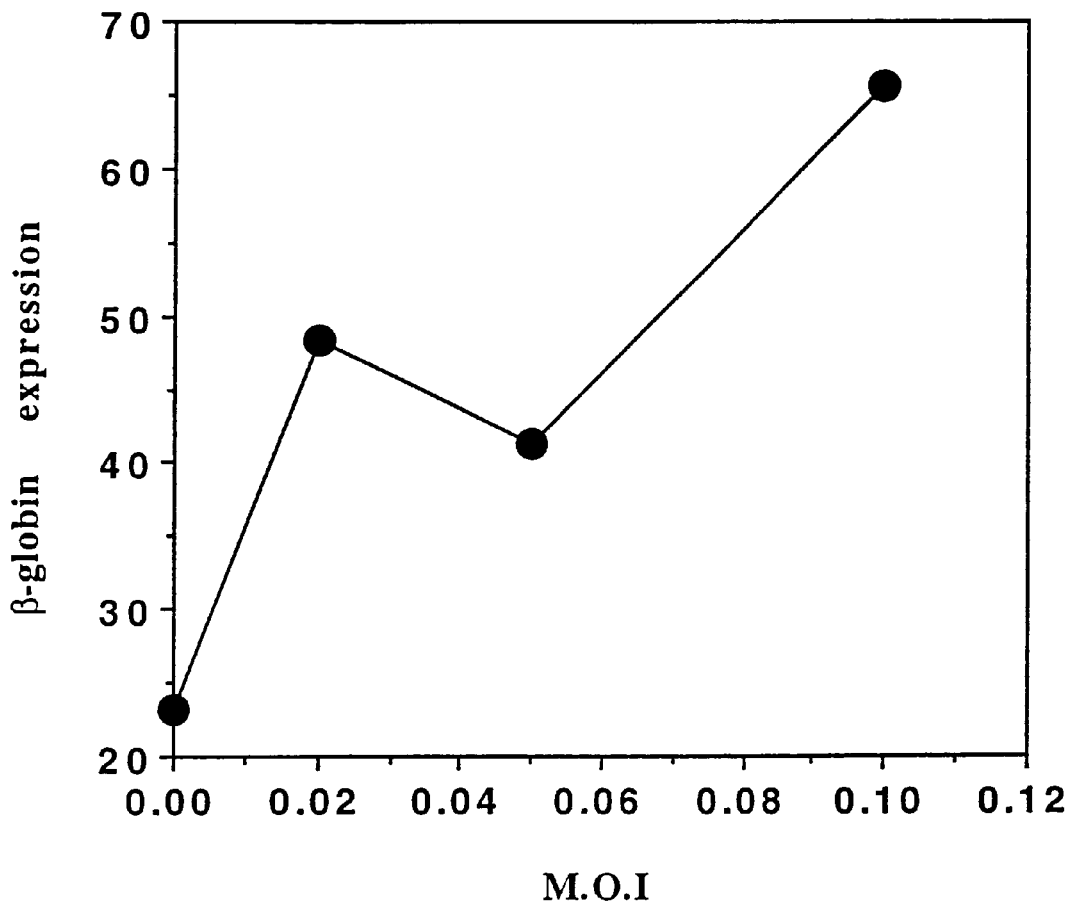
FIG. 6 is a graphic representation of the effects of m.o.i. on β-globin expression, the presented results being determined by scanning the autoradiogram of FIG. 5(b) to quantitate the β-globin expression levels.

As can be seen from FIG. 5(b), the GATA-1 signal is similar in all the RNA samples. Cultures derived from both patients show a low expression signal in the control experiments (SV40 infected and mock infection), reflecting δ-globin expression. Expression of the exogenous, normal β-globin gene is significant in both cultures. Furthermore, the level of expression depends on the m.o.i., as clearly seen in FIG. 5(b) and in FIG. 6, where different amounts of the pSO6β pseudovirions were used to infect the cell cultures to yield varying m.o.i.s. FIG. 6 shows the effect of m.o.i. on β-globin expression. The results in FIG. 6 represent a quantification of the results of FIG. 5(b) obtained by scanning the autoradiograms of FIG. 5(b). For m.o.i. of 0.02, 0.4 ml of the pseudoviral stock was used to infect $2 \times 10^5$ cells; for m.o.i. of 0.05, 1 ml of the stock was used to infect $2 \times 10^5$ cells; and for m.o.i of 0.1, 0.4 ml of 5-fold concentrated stock was used to infect $2 \times 10^5$ cells. It should be noted that the higher volume used for infections, i.e. 1 ml, in the case of m.o.i. −0.05, the volume has an adverse effect on the success of the infection, i.e. minimal volumes should be used. Together with the results shown in FIG. 5(a), those shown in FIGS. 5 and 6 indicate that normal levels of expression of the exogenous β-globin gene may be achieved by manipulating the m.o.i.

Additional experiments (not shown) support the above results. There is a low signal of the normal β-globin in the control experiments, either mock or SV40 infections, due to δ-globin expression. Infection with SOβ-9 pseudovirions consistently led to an elevated normal β-globin signal. The control assays of the endogenous β-globin (mutant) RNA and GATA-1 RNA show that the cells were not adversdely affected by the infections. Expression of the exogenous normal β-globin gene is significantly improved when part of HSII is included in the construct. (FIG. 5(a)). Furthermore, the expression is directly related to the multiplicity of infection (m.o.i.). Subtraction of the δ-globin expression background shows that increasing the m.o.i. two-fold almost doubled the expression of the exogenous gene. This suggests that infection at an m.o.i of 1–5 IU/cell, when almost every cell in the culture is infected, will yield a normal level of expression, as required for successful gene therapy.

The results demonstrate the feasibility of using the SV40/β-globin delivery system for gene therapy of β-thalassemia.

EXAMPLE 3

The SV40/MDR1 Delivery System

Several experiments using SV40/MDR1 pseudovirions to infect human and murine tissue culture cells were performed, with the goal of conferring chemotherapy resistance to chemosensitive cells.

Plasmid construction

Figure 8:
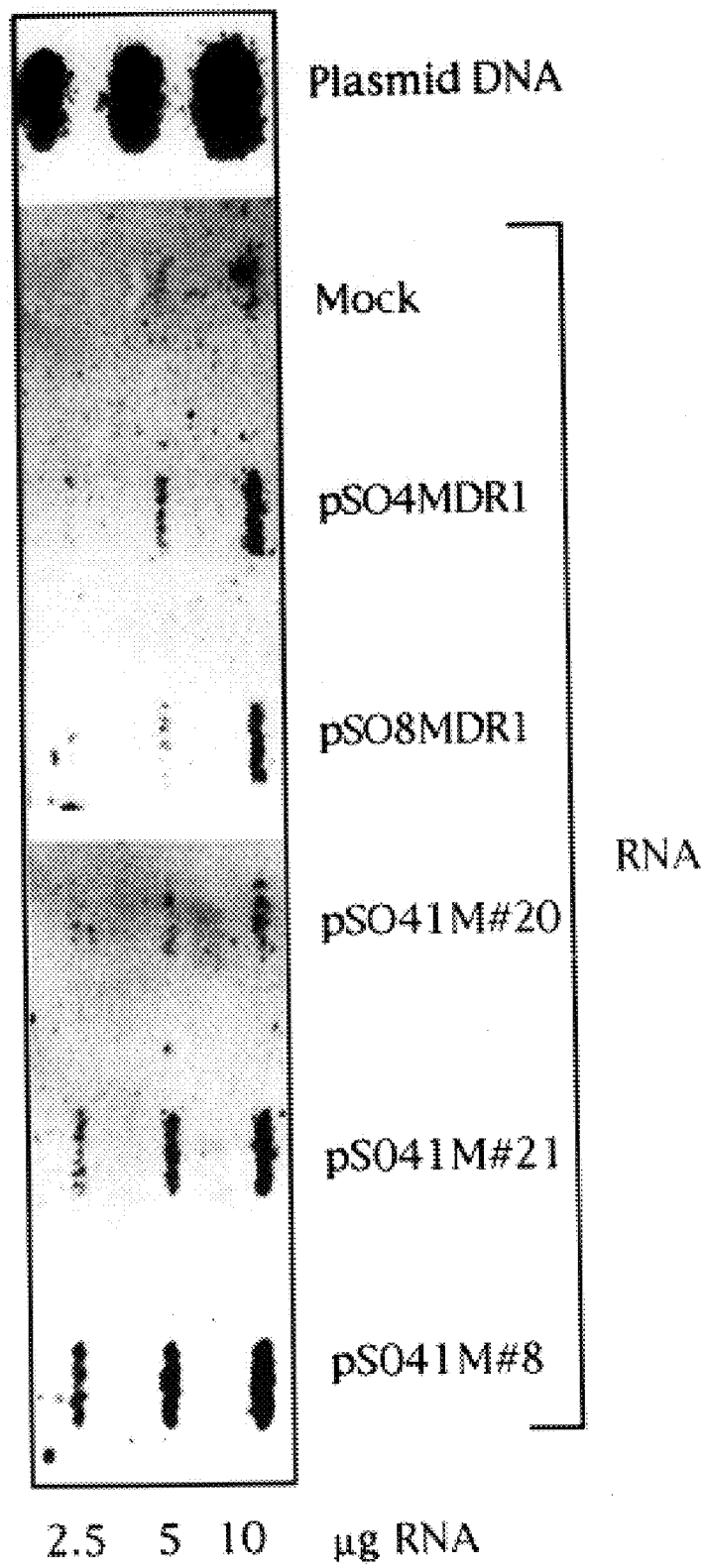
FIG. 8 Expression analysis of various SV40/MDR1 constructs. RNA was isolated from transfected CMT4 cells 2 days post transfection. The RNA was spotted at 3 concentrations on nitrocellulose membranes and hybridized to a $^{32}$P-labelled human MDR1 fragment. Plasmid DNA served as a positive control for the hybridization. Constructs pSO4MDR1 and pSO8MDR1 do not contain the SV40 polyadenylation signal, while the pSO41M constructs do. pSO41M#8 was used as a basis for further constructions.

The MDR1 cDNA was obtained from Drs. Michael Gottesman and Ira Pastan of the NIH. It was first cloned into an SV40 vector which did not contain a polyadenylation signal since the cDNA was thought to contain a functional polyadenylation signal. Transfection experiments into the monkey cell line CMT4 using these plasmids demonstrated low levels of human MDR1 RNA. New plasmids were constructed using pSO41, which carries the SV40 early polyadenylation signal. Some of these constructs showed higher level of MDR1 RNA transcription in CMT4 cells (FIG. 8).

Figure 9:
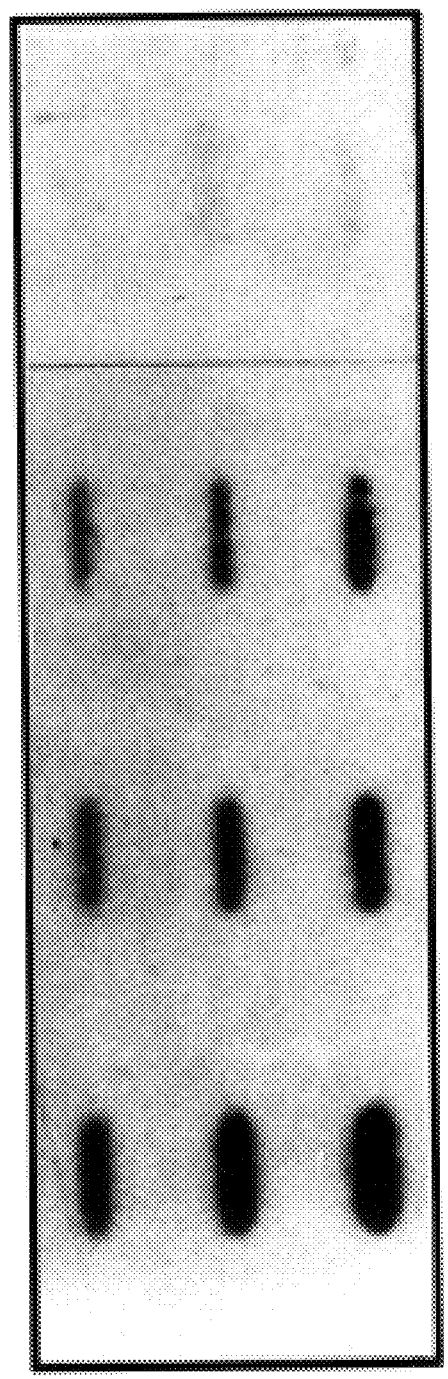
FIG. 9 Expression analysis of various pSO41M constructs. Expression studies were performed as in FIG. 8. Construct pSO41M#8 was found to contain 3 SacII sites, pSO41M#5 contains 2 SacII sites and pSO41M#10—a single SacII site. This plasmid was designated pSM1 and used in further experiments.

There were a number of additional problems with the MDR1 cDNA obtained from NIH. Multiple SacII sites were present 5' to the gene, which could create stem-loop structures, thus interfering with expression; an extra 5' noncoding region was present which may have also reduced expression. Therefore, additional plasmids were constructed. Those gave higher RNA levels in CMT4 cells. pSM41#10 in FIG. 9 was designated pSM1, and was used for further experiments. The plasmid is described in detail in FIG. 7. Plasmid pSM1 was deposited at the American Type Culture Collection under No. ATCC 97125, deposited Apr. 28, 1995, in accordance with the provisions of the Budapest Treaty.

Infection Experiments

Figure 7:
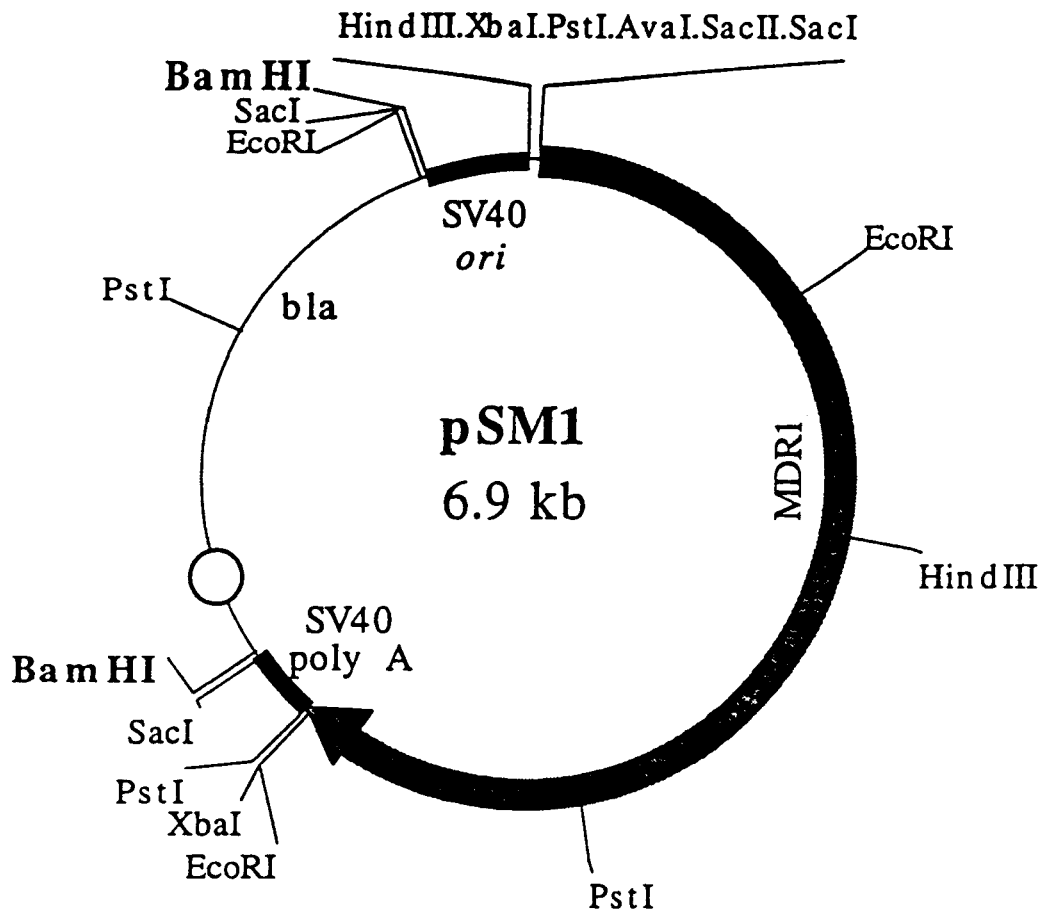
FIG. 7 is a map of pSM1. The human MDR1 cDNA (coordinates 286–4646, Genbank hummdrl.gb-pr) was cloned into the pSO41 vector, which contains the SV40 ori (SV40 coordinates 294–5171, spanning the SV40 enhancer, ses, and ori) as well as the SV40 poly(A) signal coordinates 2770–2533, including the early polyadenylation signal) and pBRM10 (pBR322 sequence coordinates 2369–4360). For preparation of pseudo-virions, the plasmid is digested at the BamHI sites, to excise bacterial sequences, and religated.

The construct pSM1 (pS41M#10 in FIG. M-3) was packaged in the sarne manner as the b-globin constructs, except that BamHI (rather than SacI) was used to excise the SV40 vector sequences and the MDR1 cDNA from the plasmid (FIG. 7). Encapsidation was performed in COS cells, using wild type SV40 as a helper. The pseudoviral titer was initially around $5 \times 10^4$ but using aquacide, was concentrated to a titer of $5 \times 10^5$ pfu/ml. The titer was determined using infection of CMT4 cells, as described for the b-globin constructs.

These pseudovirions were used to infect two different cell line. P388$^s$ is a chemosensitive mouse lymphoblastic leukemia line, which is widely used in studies on sensitivity to chemotherapy. K562, a human erythroleukemia cell line, is also sensitive to chemotherapeutic agents. K562 cells serve as a model for human hemopoietic marrow cells, which will be the target of infection in clinical studies.

Preliminary experiments indicated that both P388 and K562 were reproducibly infected by the SV40/MDR1 delivery vector, that the MDR1 cDNA was expressed, and a functional MDR1 protein was produced. The protein was assayed by using rhodamine 123 staining, as described above.

Figure 10A:
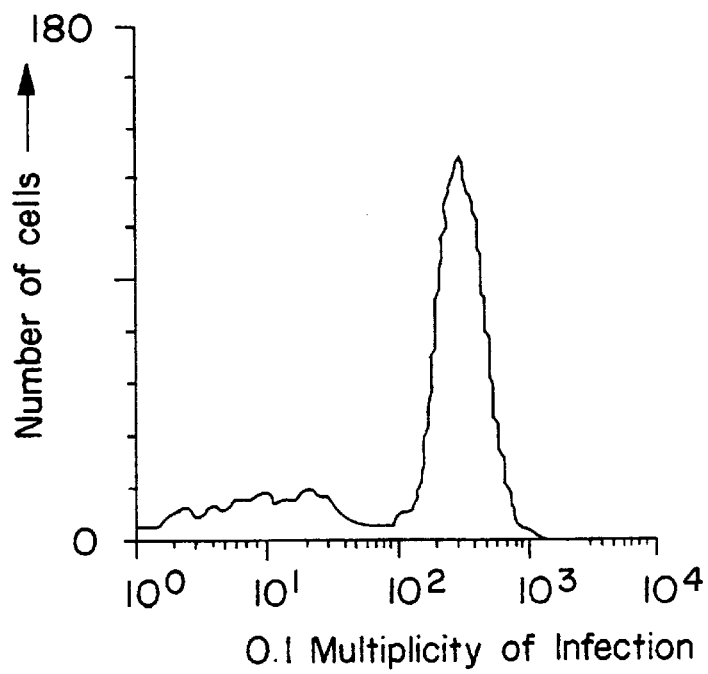
FIG. 10A shows MDR1 analysis using rhodamine 123 staining of K562 cells mock transfected at a multiplicity of infection of 0.1.
Figure 10B:
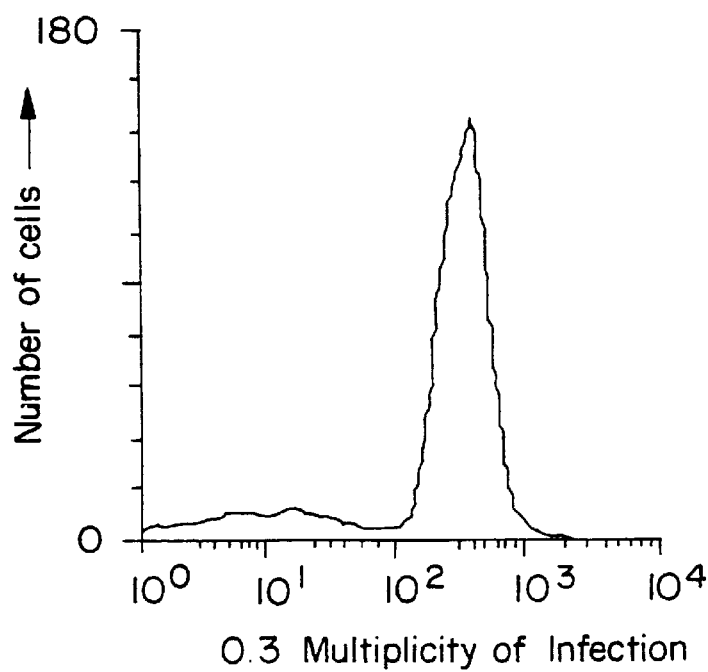
FIG. 10B shows MDR1 analysis using rhodamine 123 staining K562 cells mock transfered at a multiplicity of infection 0.3.
Figure 10C:
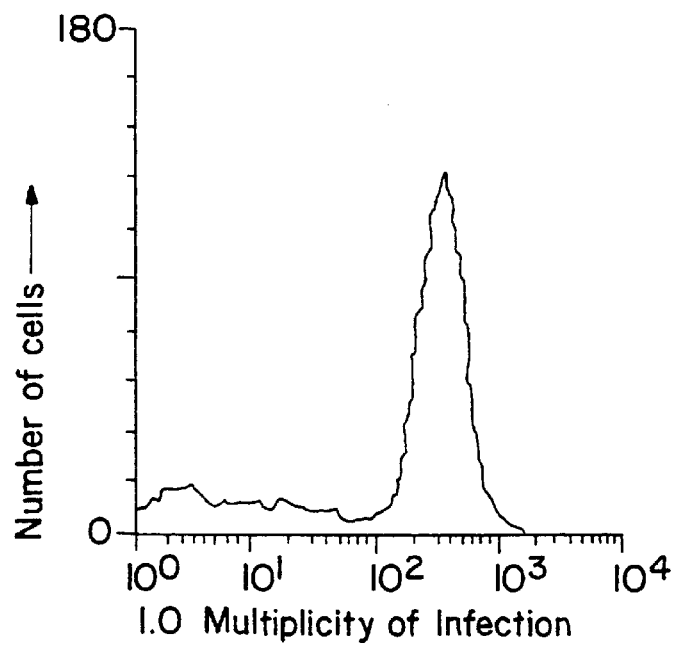
FIG. 10C shows MDR1 analysis rhodamine 123 staining of K562 cells mock transfected at a multiplicity of infection of 1.0.
Figure 10D:
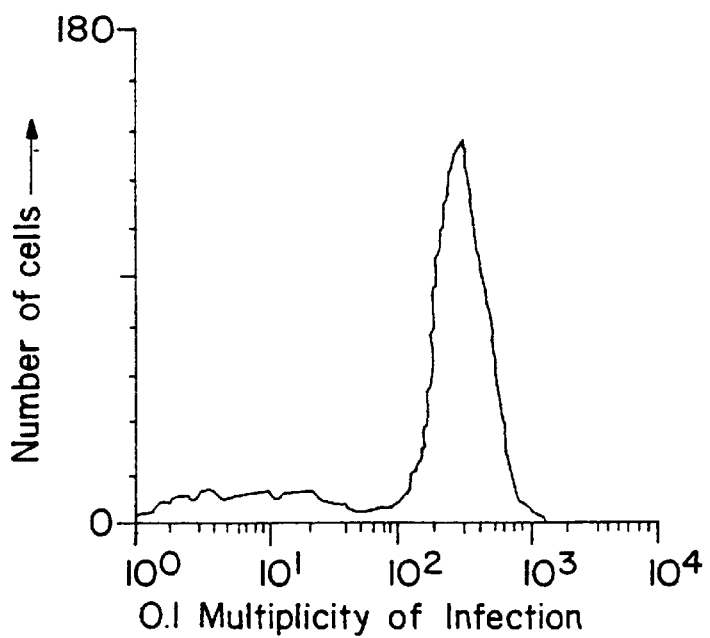
FIG. 10D shows analysis using rhodamine 123 staining of K562 cells tranfected with wild type SV40 at a multiplicity of infection of 0.1.
Figure 10E:
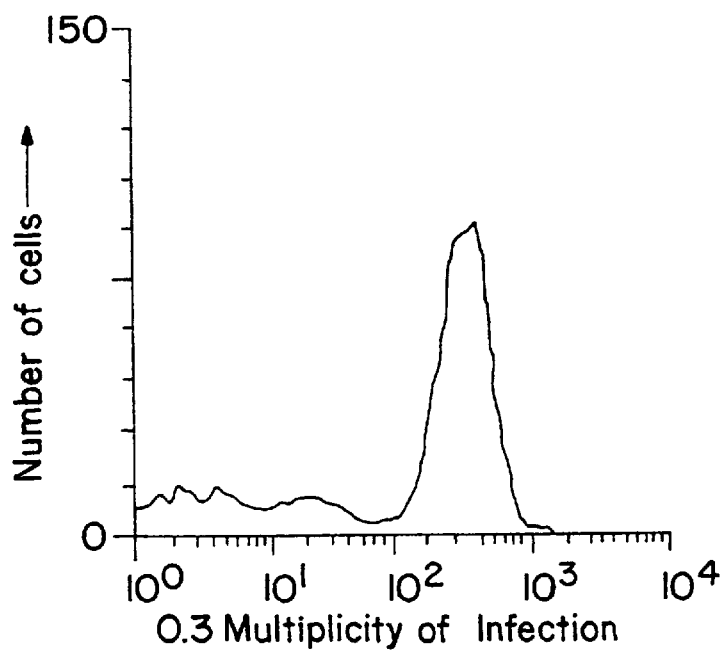
FIG. 10E shows MDR1 analysis using rhodamine 123 staining of K562 cells trasfected with wild type SV40 at a multiplicity of infection of 0.3.
Figure 10F:
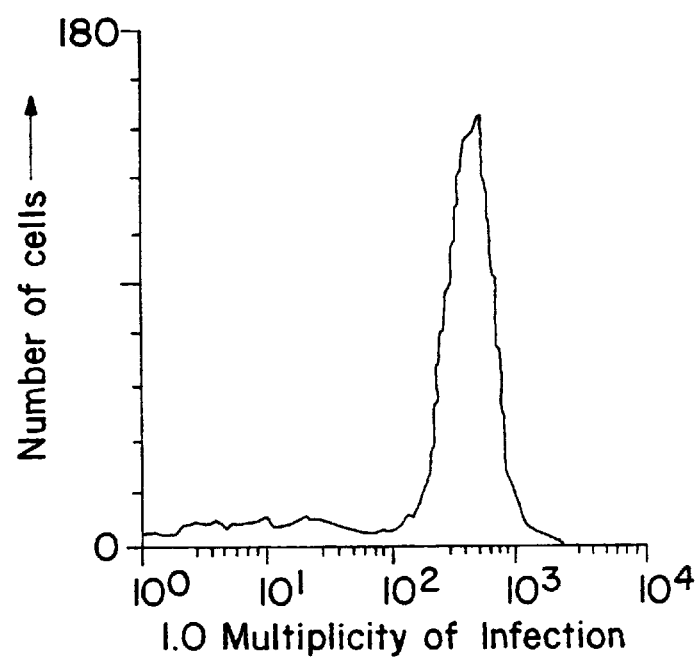
FIG. 10F shows MDR1 analysis using rhodamine 123 staining of K562 cells tranfected with wild type SV40 at a multiplicity of infection of 1.0.
Figure 10G:
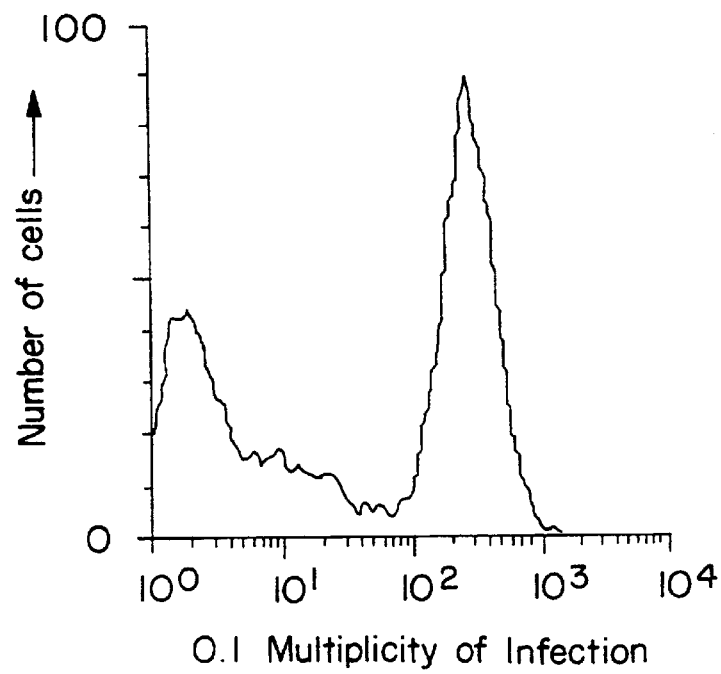
FIG. 10G shows MDR1 analysis using rhodamine 123 staining of K562 cells transfected with SV40/SM1 pseudovirions at a multiplicity of infection of 0.1.
Figure 10H:
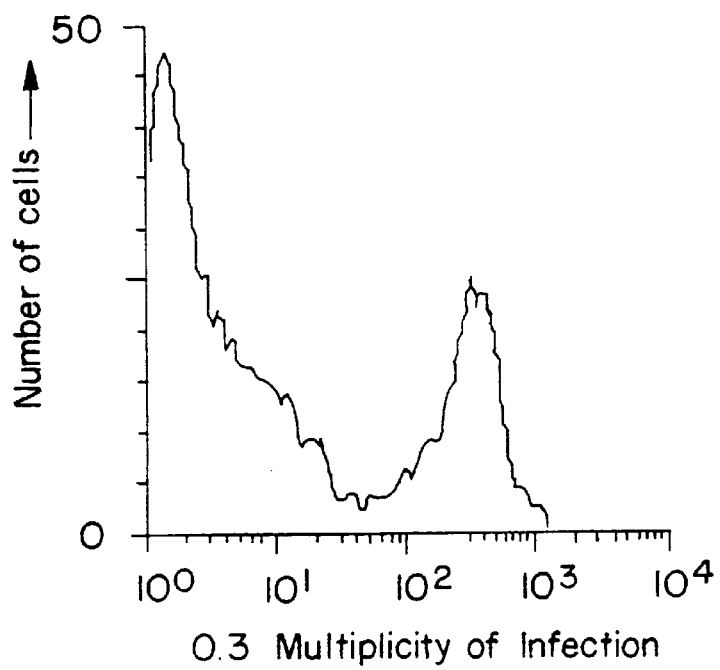
FIG. 10H shows MDR1 analysis using rhodamine 123 staining of K562 cells transfected with SV40/SM1 pseudovirions at a multiplicity of infection of 0.3.
Figure 10:
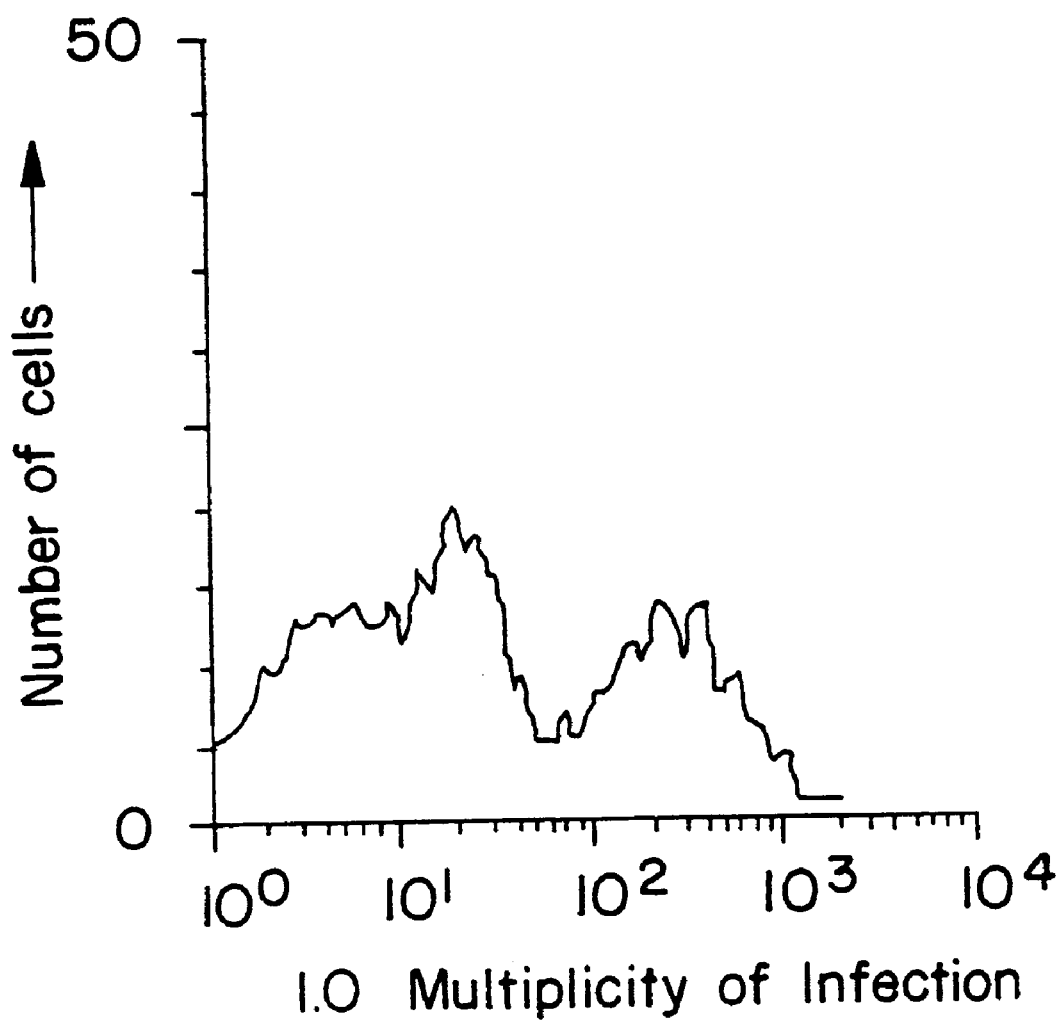
FIG. 10I shows MDR1 analysis using rhodamine 123 staining of K562 cells trasfected with SV40/SM1 pseudovirions at a multiplicity of infection of 1.0.

A detailed experiment was performed with K562 cells. The cells were infected with SV40/SM1 pseudovirions at three different multiplicities 0. 1, 0.3, 1.0. As a control, since SV40 was present in the pseudoviral mixture, cells were also infected with SV40 wild type at the same multiplicities. Mock infection served as an additional control. After 72 hours, presence of functional MDR1 protein was analyzed using the rhodamine 123 staining method. FACS analysis is used to determine the number of bright and dull-staining cells, as seen in FIG. 10. Most of the mock infected cells (FIGS. (10A–10C) were present in a single peak of cells brightly stained with rhodamine 123, indicating no MDR1 activity. In the SV40/SM1 infections (FIGS. (10C and 10I) some of the cells appear as a dull-staining population (the peak on the left side of the panels). These results indicate the presence of a functional MDR1 protein in the infected cells. The number of the dull-stained cells increases with the increase in the multiplicity of infection. The control infections with SV40 wild type did not result in the appearance of rhodamine-dull population (FIGS. 10D–10F).

Figure 11:
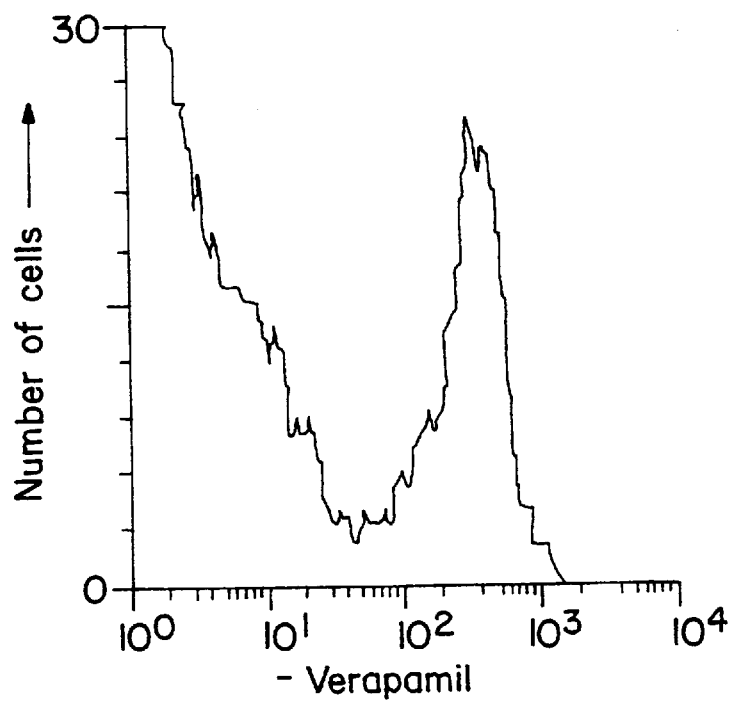
FIG. 11A shows MDR1 activity on cells infected with SV40 at a multiplicity of 0.3 in the absence of verapmil.
FIG. 11B shows MDR1 activity on cells infected with SV40 at a multiplicity of 0.3 in the presence of verapmil.
FIG. 11C shows MDR activity on cells infected with SV40/SM1 at a multiplicity of 0.3 in the absence of verapmil.
FIG. 11D shows MDR activity on cells infected with SV40/SM1 at a multiplicity of 0.3 in the presence of verapmil.
Figure 11:
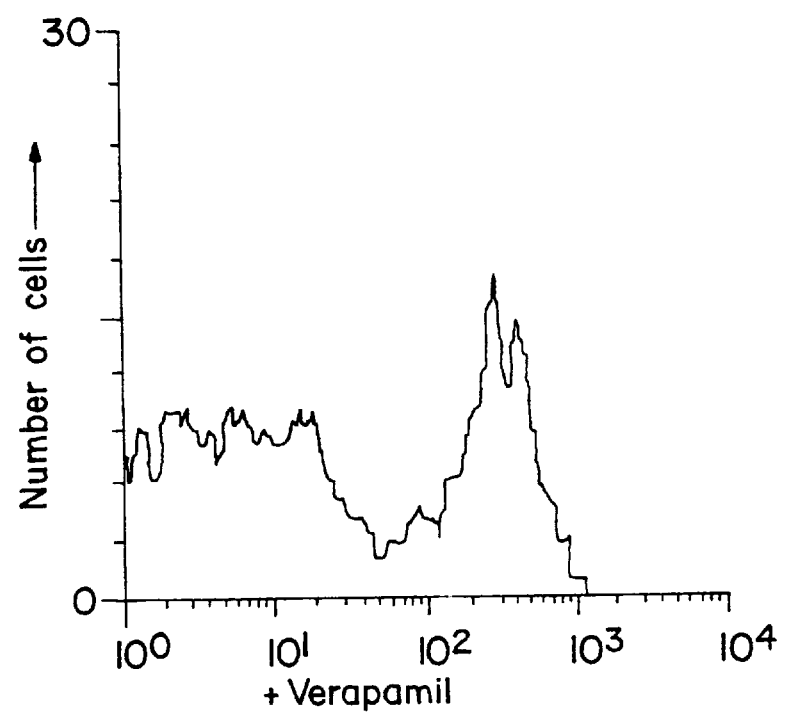

To confirm that MDR1 is responsible for the shift in the rhodamine staining characteristics of the cells, verapamil, an inhibitor of MDR1, was used. As seen in FIG. 11, the addition of verapamil inhibited the appearance of the dull staining cells in the SV40/MDR1 infection (FIGS. 11C and 11D). However, the small dull staining population in the SV40 control infection (FIGS. 11A and 11B) was not affected, indicating that the dull staining of those cells was not due to MDR1 activity.

These results demonstrate that 1- The construct pSM1 can be packaged into infectious SV40 pseudovirions; 2- The SV40/MDR1 pseudovirions are capable of conferring multidrug resistance upon infected human cells. This demonstrates that the MDR1 cDNA has entered into the cells and is expressed.

EXAMPLE 4

The SV40/APO A-I Delivery System

The feasibility of using the SV40 delivery system for the introduction and expression of the human APO A-I cDNA was investigated.

Figure 12:
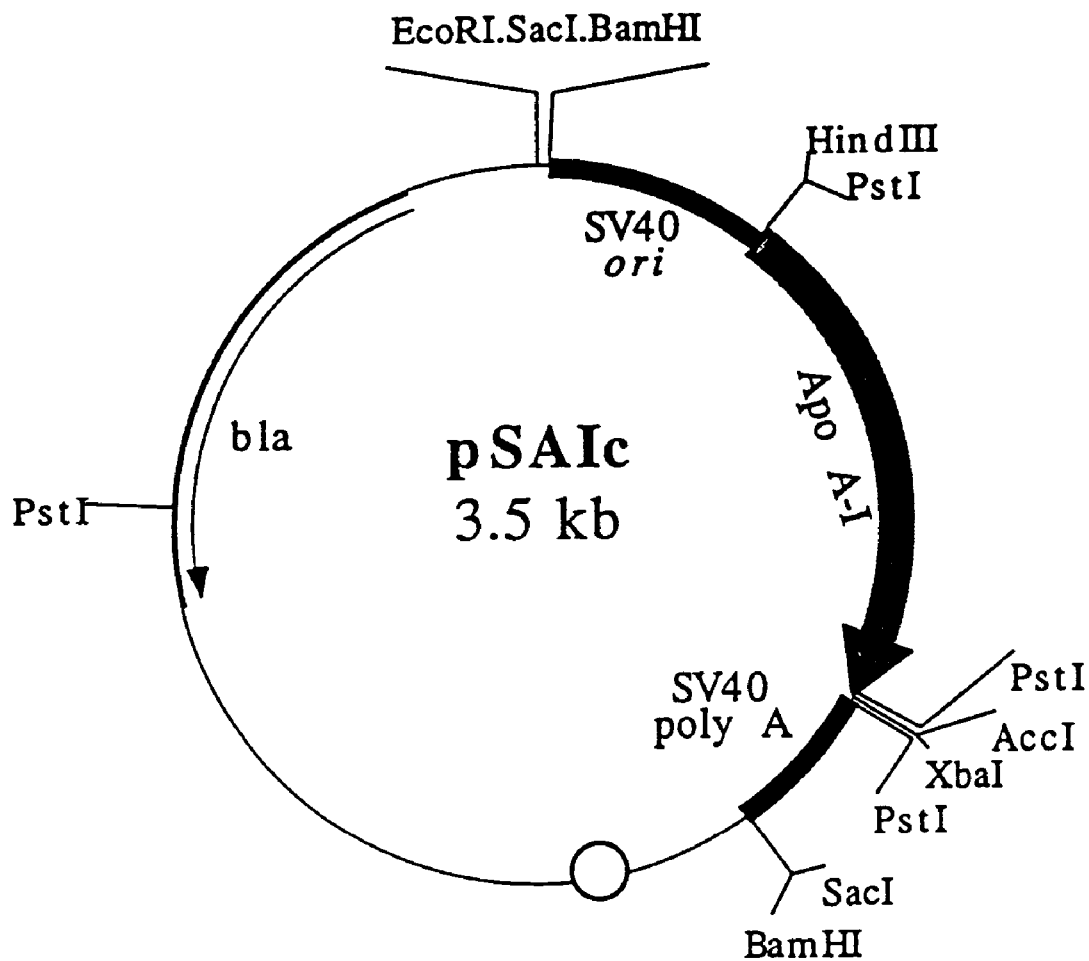
FIG. 12 Structure of pSAIc. Human APO A-I cDNA was cloned for expression in the vector pSO41 between the SV40 regulatory region and the early SV40 polyadenylation signal.

The full size human APO A-I cDNA, encoding for apolipoprotein A-I, was constructed by ligating two partial cDNA clones in pUC19: the 5' part was derived from pAI-121 [Karathanasis, S. K., et al., Proc. Nati. Acad. Sci. USA (1983) 80:6147–6151] and the 3' part from pAI-101 [Karathanasis et al., ibid]. These parts were fused at the unique BalI site. The full cDNA was transferred into the vector pSO41 using the HindIII and XbaI sites, generating plasmid pSAIc (FIG. 12). Plasmid pSAIc was deposited at the American Type Culture Collection under ATCC No. 97127 in accordance with the provisions of the Budapest Treaty.

Plasmid pSAIc was first tested for expression in 293 cells, a human cell-line transformed by DNA fragments of human adeno type 5 virus [Graham, F. L. and Nairn R. J. Gen. Virol. (1977) 36:59–72]. The cells were transfected with pSAIc DNA using the calcium phosphate precipitation technique. After the transfection (16 hrs) the cells were washed and incubated for additional 24 hours with DMEM medium without serum. As APO A-I is expected to be secreted to the medium, the medium was collected and concentrated about 100 fold with aquacide (purchased from CalBiochem). The concentrated medium was assayed for APO A-I protein by the "rocket" immunoelectrophoresis assay, with anti-human APO A-I polyclonal antibodies raised in rabbits, as previously described [Chajek-Shaul, T., et al., Proc. Natl. Acad. Sci. USA (1991) 88:6731–6735]. The results showed presence of the human APO A-I, indicating that the gene was expressed, the protein was produced and secreted to the medium. By comparison with a known standard, the level of APO A-I protein was estimated as 62 ng/ml.

pSAIc was packaged as pseudovirions as previously described for pSO3cat [Oppenheim, A., et al., Proc. Natl. Acad. Sci. USA (1986) 83:6925–6929]. The pseudoviral titer was $4.5 \times 10^5$ pfu/ml. The pseudovirions were used to infect COS cells at a multiplicity of infection of 0.2. The infected cultures were incubated with and without 10% FBS. Medium was collected after 24 and 48 hrs, concentrated about 200–300 fold with aquacide and assayed for APO A-I protein by the rocket immunoelectrophoresis assay . APO A-I protein was present both at 24 and at 48 ahrs after the infection, at levels of about 33 ng/ml for each sample, estimated by comparison with a standard control. No protein was seen in the mock-infected cells.

After 48 hrs the cultures were harvested and RNA was purified by the acid guanidium thiocyanate procedure [Chomczynsky, P. and Sacchi, N. Anal. Biochem. (1987) 162:156–159]. The RNA was spotted on a nitrocellulose membrane at 3 concentrations (3, 1.5 and 0.75 mg/slot) and hybridized to an APO A-I-specific probe (HindIII-XbaI fragment, 0.9 kb long).

Figure 13:
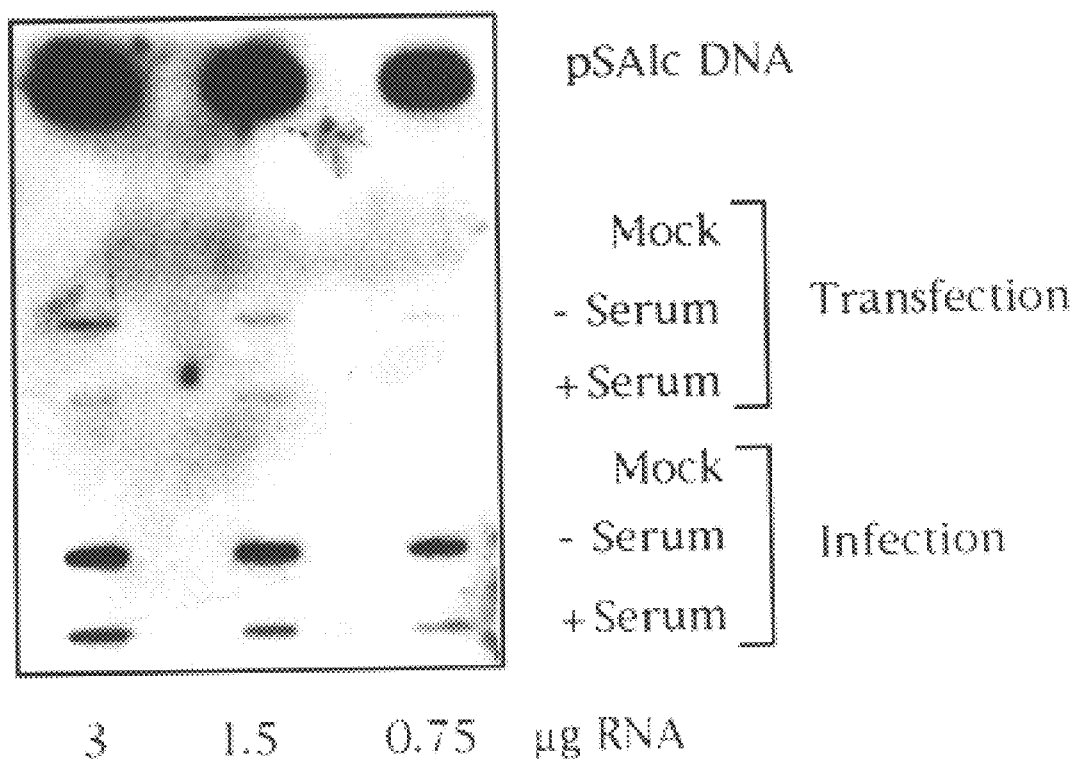
FIG. 13 Expression of SV40/APO A-I pseudovirions. RNA was extracted from COS cells, transfected with pSAIc DNA or infected with pSAIc pseudo-virions. The cultures were incubated for 2 days without serum (−serum) or in the presence of 10% FBS (+serum). The mock transfected and mock infected cultures were incubated without serum. The RNA from each culture was spotted onto the nitrocellulose membrane at 3 concentrations, as depicted. Hybridization was performed with a $^{32}$P-labelled APO A-1 cDNA fragment.

The results (FIG. 13) showed presence of APO A-I RNA in the infected cells, indicating that the APO A-I DNA entered the cells and the gene was expressed. Cells incubated without serum had substantially higher RNA levels. As seen in FIG. 13, low levels of RNA were also observed in COS cells which were transfected with pSAIc plasmid as a control experiment. In those experiments, 10 mg plasmid DNA was used to transfect 75 $cm^2$ culture, by the calcium phosphate precipitation procedure.

These results demonstrate that plasmid pSAIc can be packaged into SV40 pseudovirions, and that this delivery system is efficient in gene transfer. The delivered gene is transcribed, the APO A-I protein is produced in the infected cells and secreted.

EXAMPLE 5

Construction of Plasmid pSO41

Figure 14:
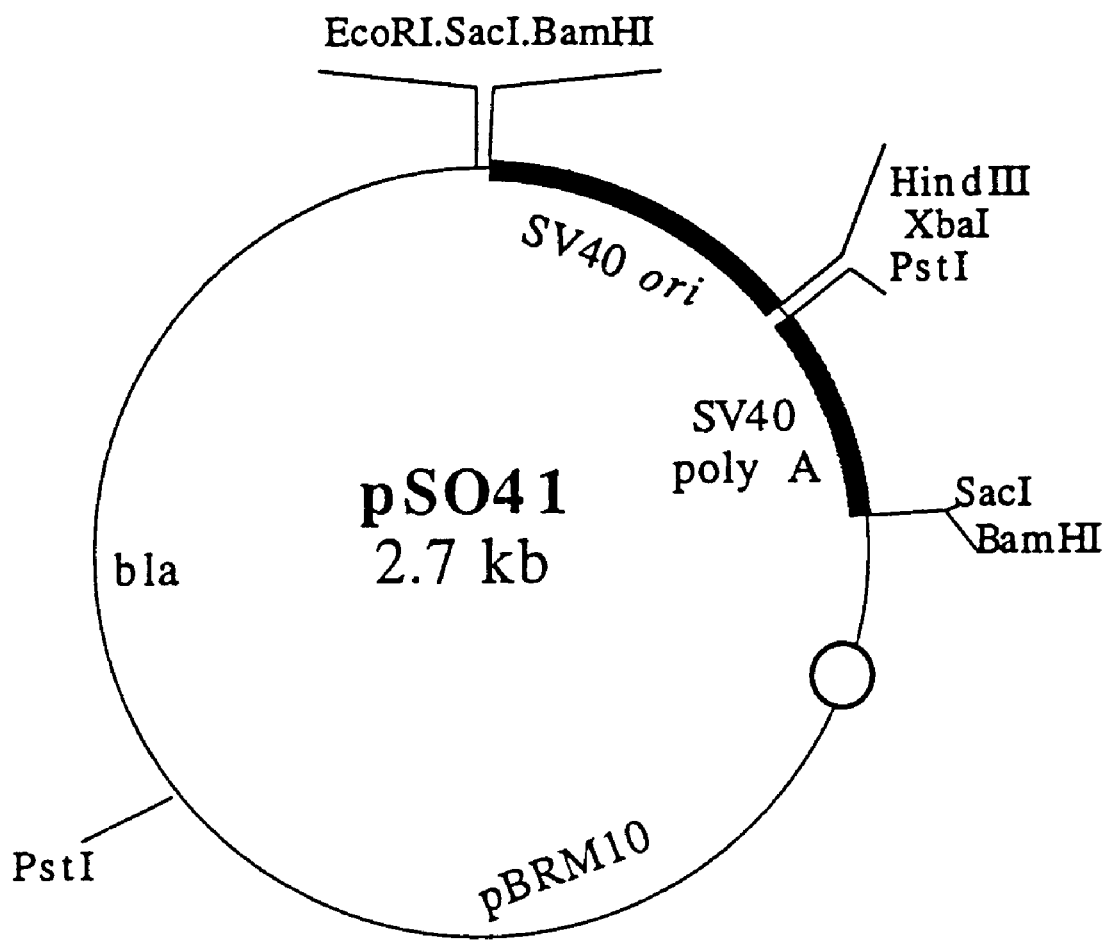
FIG. 14 shows plasmid pSO41 which carries the SV40 regulatory region from the KpnI site at coordinate 298 (replaced by a BamHI site in the construction) through the enhancer, ses, the early promotor and the ori to the HindIII site at coordinate 5172. The SV40 early polyodenulation signal is from the BclI site at coordinate 2770 to the BamHI site at coordinate 2534. Both the BclI and BamHI sites were destroyed by ligation to a BglII site. The pBRM10 sequences are from coordinate 2369 to the EcoRI site at coordinate 4360.

Plasmid pSO41 is shown in FIG. 14. The constructs are designed so that the gene of interest can be cloned between the SV40 early promoter, which is embedded in the SV40 ori region, and the SV40 polyadenylation signal. This facilitates cloning of cDNA or any open reading frame (ORF) for expression. RNA transcription is initiated at the SV40 early promoter. The polyadenylation signal serves for cleavage and polyadenylation of the transcribed RNA. Translation occurs from the translation initiation codon (ATG) in the cloned cDNA, or from an ATG introduced in frame at the beginning of the cloned ORF.

The experiments with the MDR1 gene (Example 3) demonstrate that the addition of the polyadenylation signal substantially improved expression of the cloned gene.

Deposit information pSO41 is deposited at the ATCC under Accession No. 97126.

pSO6β-9 is deposited at the ATCC under Accession No. 75596.

pSM1 is deposited at the ATCC under Accession No. 97125.

pSAIc is deposited at the ATCC under Accession No. 97127.

The current address of the depository is American Type Cullture Collection (ATCC), 10801 University Boulevard, Manassas, Va. 20110-2209; Phone No. 703-365-2700.

We claim:

1. A DNA construct comprising pSO41 operably linked to an exogenous DNA sequence encoding a protein, wherein said pSO41 is deposited at the ATCC under Accession No. 97126.

2. A DNA construct according to claim 1 wherein said exogenous DNA sequence comprises a DNA sequence encoding all or a biologically active fragment of p-glycoprotein.

3. A DNA construct according to claim 1 wherein said protein is selected from the group consisting of enzymes, receptors, structural proteins, regulatory proteins and hormones.

4. A DNA construct according to claim 1, further comprising a transcription enhancer suitable for expression of said protein in mammalian cells.

5. A DNA construct according to claim 1, further comprising an SV40 transcription enhancer.

6. A DNA construct according to claim 1, comprising a DNA sequence encoding at least one selectable marker.

7. A DNA construct according to claim 6 wherein said selectable marker is selected from the group consisting of: the bacterial hygromycin B phosphotransferase gene, hyg; the bacterial neomycin resistance gene, neo; the mammalian multidrug resistance gene, mdr 1; and the mammalian dihydrofolate reductase gene, dhfr.

8. A DNA construct according to claim 1, comprising a DNA sequence encoding all or a biologically active fragment of the human apolipoprotein A-I.

9. A DNA construct comprising pSO41, deposited at the ATCC Under Accession No. 97126.

10. An SV40 pseudovirus containing a DNA construct comprising pSO41 operably linked to an exogenous DNA sequence encoding a protein, wherein pSO41 is deposited at the ATCC under Accession No. 97126.

11. A transduced, isolated mammalian cell having integrated into its genome the DNA construct comprising pSO41 operably linked to an exogenous DNA sequence encoding a protein, wherein pSO41 is deposited at the ATCC under Accession No. 97126.

12. A cell according to claim 11, wherein said exogenous DNA sequence is selected from the group consisting of DNA which encodes a protein which is not made or contained in the said cell; DNA which encodes a protein which is made or contained in said cell in abnormally low amounts or in a defective form; and DNA which encodes a protein which is made or contained in said cell in physiologically normal amounts.

13. A cell according to claim 11, wherein the cell is selected from the group consisting of hemopoietic cells, epithelial cells, endothelial cells, liver cells, epidermal cells, muscle cells, fibroblasts, tumor cells, and germ line cells.

14. A hemopoietic cell according to claim 13 wherein the cell is selected from the group consisting of bone marrow cells, peripheral blood cells, cord blood cells and liver cells.

15. A DNA construct comprising pSO6β-9 deposited at the ATCC under Accession No. 75596.

16. A DNA construct according to claim 15 further comprising a DNA sequence encoding at least one selectable marker.

17. A DNA construct according to claim 16 wherein said selectable marker is selected from the group consisting of: the bacterial hygromycin B phosphotransferase gene, hyg; the bacterial neomycin resistance gene, neo; the mammalian multi-drug resistance gene, mdr 1; and the mammalian dihydrofolate reductase gene, dhfr.

18. An SV40 pseudovirus containing a DNA construct comprising pSO6β-9, deposited at the ATCC under Accession No. 75596.

19. A transduced isolated mammalian hematopoietic cell having integrated into its genome a DNA construct comprising pSO6β-9, deposited at the ATCC under Accession Number 75596, wherein pSO6β-9 comprises an exogenous DNA sequence encoding β-globin.

20. A cell according to claim 19 selected from the group consisting of bone marrow cells and peripheral blood stem cells.

21. A DNA construct, SO6β-9, constructed by removing the pBR322 sequences from pSO6β-9, wherein pSO6β-9 is deposited at the ATCC under accession No. 75596.

22. An SV40 pseudovirus containing a DNA construct comprising SO6β-9, constructed by removing the pBR322 sequences from pSO6β-9, wherein pSO6β-9 is deposited at the ATCC under Accession No. 75596.

23. A transduced, isolated mammalian cell having integrated into its genome a DNA construct comprising SO6β-9, wherein SO6β-9 is constructed by removing the pBR322 sequences from pSO6β-9, wherein pSO6β-9 is deposited at the ATCC under Accession No. 75596.

24. A DNA construct comprising pSM1, deposited at the ATCC under Accession No. 97125.

25. An SV40 pseudovirus containing a DNA construct comprising pSM1, deposited at the ATCC under Accession No. 97125.

26. A transduced, isolated mammalian hematopoictic cell having integrated into its genome a DNA construct comprising pSM1, deposited at the ATCC under Accession No. 97125, wherein pSM1 comprises an exogenous DNA sequence encoding p-glycoprotein.

27. A DNA construct comprising pSAIc, deposited at the ATCC under Accession No. 97127.

28. An SV40 pseudovirus containing a DNA construct, pSAIc deposited at the ATCC under Accession No. 97127.

29. A transduced, isolated mammalian cell having integrated into its genome a DNA construct comprising pSAIc, deposited at the ATCC under Accession No. 97127, wherein pSAIc comprises an exogenous DNA sequence encoding apolipoprotein.

* * * * *

UNITED STATES PATENT AND TRADEMARK OFFICE
CERTIFICATE OF CORRECTION

PATENT NO. : 6,090,608
DATED : July 18, 2000
INVENTOR(S) : Ariella Oppenheim, et al.

It is certified that error appears in the above-identified patent and that said Letters Patent is hereby corrected as shown below:

On the front page of the patent, in item [75], delete "Toba" and add therefore ---Tova---.

Signed and Sealed this

Seventeenth Day of April, 2001

Attest:

NICHOLAS P. GODICI

Attesting Officer                Acting Director of the United States Patent and Trademark Office